United States Patent [19]

Inoue et al.

[11] Patent Number: 4,889,953
[45] Date of Patent: Dec. 26, 1989

[54] GLYCEROL DERIVATIVES, THEIR PRODUCTION AND USE

[75] Inventors: Keizo Inoue, Tokyo; Hiroaki Nomura; Tetsuya Okutani, both of Osaka, all of Japan

[73] Assignee: Takeda Chemical Industries, Ltd., Osaka, Japan

[21] Appl. No.: 76,527

[22] Filed: Jul. 22, 1987

[30] Foreign Application Priority Data

Jul. 22, 1986 [JP] Japan .................................. 61-173227
Mar. 5, 1987 [JP] Japan .................................. 62-51049

[51] Int. Cl.$^4$ ............................................. C07C 93/04
[52] U.S. Cl. .................................... 564/293; 544/160;
544/162; 544/163; 544/167; 544/169; 544/170;
544/171; 544/173; 544/174; 544/175; 544/177;
544/224; 544/239; 544/382; 544/384; 544/390;
544/398; 544/399; 544/401; 546/139; 546/141;
546/143; 546/146; 546/147; 546/149; 546/152;
546/153; 546/157; 546/162; 546/169; 546/171;
546/174; 546/176; 546/177; 546/179; 546/180;
546/216; 546/224; 546/225; 546/230; 546/232;
546/235; 546/236; 546/237; 546/238; 546/240;
546/242; 546/243; 546/244; 546/245; 546/246;
546/248; 546/300; 546/301; 546/302; 546/305;
546/306; 546/312; 546/315; 546/316; 546/323;
546/330; 546/331; 546/334; 546/335; 546/338;
546/339; 546/340; 546/341; 546/344; 548/186;
548/187; 548/196; 548/200; 548/203; 548/204;
548/213; 548/214; 548/225; 548/228; 548/229;
548/233; 548/235; 548/236; 548/243; 548/245;
548/246; 548/247; 548/248; 548/537; 548/550;
548/551; 549/551; 549/554; 549/558; 549/559;
549/560; 549/561; 558/234; 558/440; 558/444;
558/447; 560/22; 560/39; 560/156; 560/170;
560/174; 560/178; 560/251; 560/252;
260/501.13; 562/437; 562/444; 562/567;
564/284; 564/285; 564/287; 564/294; 564/441;
564/443; 564/502; 564/505

[58] Field of Search ................ 564/293, 284, 285, 287,
564/294, 441, 442, 443, 502, 505; 544/160, 162,
163, 167, 169, 170, 171, 173, 174, 175, 177, 239,
224, 382, 384, 390, 398, 399, 401; 546/139, 141,
143, 146, 147, 149, 152, 153, 157, 162, 169, 171,
174, 176, 177, 179, 180, 216, 224, 225, 230, 232,
235, 236, 237, 238, 240, 242, 243, 244, 245, 246,
248, 300, 301, 302, 305, 306, 312, 315, 316, 323,
330, 331, 334, 335, 338, 339, 340, 341, 344;
548/186, 187, 196, 200, 203, 204, 213, 214, 225,
228, 229, 233, 235, 236, 243, 245, 246, 247, 248,
537, 550, 551, 556, 557, 558, 569, 571, 573, 574;
549/551, 554, 558, 559, 560, 561; 558/234, 440,
444, 447; 560/22, 39, 156, 170, 251, 252, 174,
178; 260/501.13; 562/437, 444, 567

[56] References Cited

FOREIGN PATENT DOCUMENTS

| | | |
|---|---|---|
| 0094586 | 11/1983 | European Pat. Off. |
| 0109255 | 5/1984 | European Pat. Off. |
| 0142333 | 5/1985 | European Pat. Off. |
| 1575545 | 9/1980 | United Kingdom |
| 1583661 | 1/1981 | United Kingdom |

*Primary Examiner*—Bruce D. Gray
*Attorney, Agent, or Firm*—Wegner & Bretschneider

[57] ABSTRACT

Compounds of the formula:

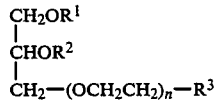

wherein $R^1$ is a higher alkyl group which may be substituted; $R^2$ is a hydrogen, a lower alkyl group which may be substituted, a lower alkanoyl group which may be substituted or a lower alkylthiocarbamoyl group; $R^3$ is a primary to tertiary amino group or a quaternary ammonium group; and n is 2 or 3, and salts thereof, have antitumor activity and platelet activating factor inhibitory activity.

6 Claims, No Drawings

GLYCEROL DERIVATIVES, THEIR PRODUCTION AND USE

FIELD OF THE INDUSTRIAL APPLICATION

This invention relates to glycerol derivatives. In more detail, it relates to compounds of the formula:

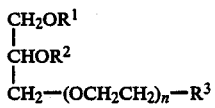

$$\begin{array}{l} CH_2OR^1 \\ |\\ CHOR^2 \\ | \\ CH_2-(OCH_2CH_2)_n-R^3 \end{array} \quad (I)$$

wherein $R^1$ is a higher alkyl group which may be substituted; $R^2$ is hydrogen, a lower alkyl group which may be substituted, a lower alkanoyl group which may be substituted or a lower alkylthiocarbamoyl group; $R^3$ is a primary, secondary or tertiary amino group or a quaternary ammonium group; and n is 2 or 3, or salts thereof, which are useful as antitumor agents and antagonists for a platelet- activating factor.

DESCRIPTION OF THE PRIOR ART

Recently it has been disclosed in scientific and patent literatures that amphipathic compounds having certain structural elements exhibit antitumor activities or antagonism to a platelet activating factor (formula III, abbreviated as PAF hereinafter). For example the gazette of Japanese Unexamined Patent Publication No.28955/1980 describes the compound of the formula II:

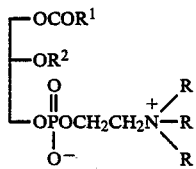

$$\begin{bmatrix} -OCOR^1 \\ -OR^2 \\ -OPOCH_2CH_2\overset{+}{N}\diagdown\overset{R}{\underset{R}{\diagup}}\\ \phantom{-OP}\underset{O^-}{\overset{\|}{O}} \end{bmatrix} \quad (II)$$

These 1-acyl-glycerol derivatives are inferior to 1-alkyl-glycerol derivatives in potency and duration of the actions because the 1-acyl group is susceptible to in vivo enzymatic hydrolysis and the compounds are deactivated. In fact, it is known that lysolecithin even at about 1000 times concentration of that of PAF cannot activate macrophages, and is much inferior to the corresponding alkylether derivative (lysoPAF) in antibody forming capacity (PFC) and in vitro and in vivo antitumor activities. A natural phospholipid of the formula III:

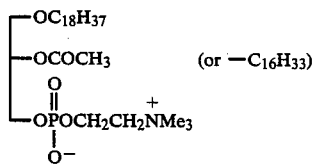

$$\begin{bmatrix} -OC_{18}H_{37} \\ -OCOCH_3 \quad (or\; -C_{16}H_{33}) \\ -OPOCH_2CH_2\overset{+}{N}Me_3 \\ \phantom{-OP}\underset{O^-}{\overset{\|}{O}} \end{bmatrix} \quad (III)$$

that is, PAF was discovered relatively recently, which has attracted attention as an important mediator in organisms such as in inflammation and blood pressure control. C. A. Demopoulos, R. N. Pinckard, and D. J. Hanahan, J. Biol. Chem., 254, 9355 (1979); J. Benveniste, M. Tence, P. Varenne, J. Bidault, C. Boullet, and J. Polonsky, C. R. Acad. Sci. (D), 289, 1037 (1979).

Phospholipids which are structurally related with PAF are known to have actions similar to those of PAF, although to a greater or lesser extent, such as platelet-activating, neutrophil- activating, tissue-impairing, vessel permeability-enhancing, and blood pressure-lowering actions. [J. T. O'Flaherty et al. Res. Commun. Chem. Pathol. & Pharmacol. 39, 291 (1983); P. Hdrary, Thrombosis Res. 30, 143 (1983)]. The alkyllysophospholipid of the formula IV is known to have antitumor actions, unlike PAF and 1-octadecyl-2-arachidonoyl-glycerophosphocholine which is known to be a PAF precursor. [W. E. Berdel, W. R. E. Bausert, U. Fink, K. Rostetter, and P. G. Munder, Anticancer Research, 1, 345 (1981). [the gazette of Japanese Unexamined Patent Publication No. 134027/1977]. However this compound (IV) is known to have also PAF-like actions such as serotonin liberation, bronchial constriction, platelet aggregation, and blood pressure lowering, due to its PAF-related structure. [the report of O'Flaherty cited above, D. J. Hanahan et al. Biochem. Biophys. Res. Commun. 99, 183 (1981)]. Therefore the compound (IV) may cause not only blood pressure lowering but also circulatory disorders such as cerebral thrombosis and angina pectoris and asthma. In addition the compound (IV) may cause topically irritating actions. These side effects restrict the possibility of clinical use of the said compound.

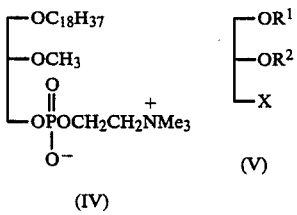

$$\begin{bmatrix} -OC_{18}H_{37} \\ -OCH_3 \\ -OPOCH_2CH_2\overset{+}{N}Me_3 \\ \phantom{-OP}\underset{O^-}{\overset{\|}{O}} \end{bmatrix} \quad \begin{bmatrix} -OR^1 \\ -OR^2 \\ -X \end{bmatrix}$$

$$(IV) \qquad\qquad (V)$$

Recently glycerides having no phosphate group represented by the formula V, wherein $R^1$=long chain alkyl, $R^2$=short chain or long chain alkyl or acyl having 2-5 carbon atoms, $X=O(CH_2)_n\text{-}R^3$, and n=an integer of 1-12, was disclosed to exhibit antagonism to PAF, and to be possibly used as a therapeutic agent for disorders due to PAF, such as anaphylactic shock. [the gazette of Japanese Unexamined Patent Publication No. 100544/1985; the gazette of Japanese Unexamined Patent Publication No. 198445/1983; T. Miyamoto et al., Kyoto Conference of Prostaglandins, Nov. 26–28, 1984, Abst. p99]. For practical use, further improvement is required in duration of the actiohs and therapeutic index. Moreover, the antitumor actions have not yet been disclosed concretely.

PROBLEMS TO BE SOLVED BY THE INVENTION

Nowadays it is shown that abnormal proliferation of carcinoma cells is derived from the structural and functional abnormalities of the membrane of carcinoma cells. On the other hand, recent studies on biomembranes have gradually shown that amphipathic lipids affect biomembranes and therefore may exert various influences on cellular metabolism and functions through the membranes. The present inventors believe that among amphipathic lipids having certain structural elements there exist those which have action sites on the membrane of carcinoma cells and can take part in control of the activities of functional protein of the membrane of carcinoma cells (for example, inhibition of enzymes involved in biosynthesis of membraneous phospholipids).

Tumor cells are known to be generally inferior to normal cells in breaking ether linkage of alkyl ether lipids. [Wykle, R. L. and Snyder, F., The Enzymes of Biological Membranes, Martonosi, A., Ed., vol. 2, Plenum Press, N.Y., 1976, 87; Lin, H. J., Ho, F. C. S., and Lee, C. L. H., Cancer Res., 38, 946 (1978); Modolell, M., Andreesen, R., Pahlke, W., Brugger, U., and Munder, P. G., Cancer Res., 39, 4681 (1979)].

That is, alkylether lipids are accumulated in tumor tissues, whereas the alkyl ether lipids are degraded and inactivated more rapidly in normal cells. The inventors believe that the compounds of the general formula I having many ether linkages inhibit selectively multiplication of carcinoma cells rather than that of normal cells. As a result of the studies, the glycerol derivatives represented by the general formula I have been found to have extremely useful antitumor actions. The compounds of the general formula I have neither platelet-aggregating nor blood pressure-lowering actions, the side effects being diminished. Since, on the contrary, the compounds exhibit antagonism to PAF, the compounds have been found to be also useful for prevention and treatment of PAF-mediated circulatory disorders and allergy.

MEANS TO SOLVE THE PROBLEMS

In the general formula I described above, the higher alkyl group represented by $R^1$ includes straight-chain alkyl groups having 8–22 carbon atoms (preferably 12–20 carbon atoms), such as n-octyl, n-nonyl, n-decyl, n-undecyl, n-dodecyl, n-tetradecyl, n-hexadecyl, n-octadecyl, and n-eicosanyl, and branched-chain alkyl groups having 8–22 carbon atoms (preferably 12–20 carbon atoms), such as 18,18-dimethylnonadecyl, 19,19-dimethyleicosyl, 19-methyleicosyl and 3,7, 11,15-tetramethylhexadecyl. The said higher alkyl group may have about 1–7 substituents such as cycloalkyl, aryl, halogen, cyano, ethynyl, 1-propynyl, oxo, and lower alkoxy. The said lower alkoxy group includes alkoxy groups having 1–4 carbon atoms such as methoxy and ethoxy. The said cycloalkyl group includes 3- to 8-membered cycloalkyl groups such as cyclopentyl and cyclohexyl. The said aryl group includes phenyl, and the said phenyl group may be substituted with lower ($C_{1-4}$)alkyl, lower($C_{1-4}$)alkoxy, hydroxy, nitro, or halogen. Halogen as a substituent of the higher alkyl group mentioned above and halogen as a substituent of the phenyl group mentioned above include fluorine, bromine, and chlorine. When $R^1$ is a substituted higher alkyl group, the position of substitution may be any substitutive position of the higher alkyl group, but ω(omega) position is preferable. The said substituted higher alkyl group includes 13-cyclopentyltridecyl, 12-cyclohexyldodecyl, 12-phenyldodecyl, octadecan-17-ynyl, hexadecan-14-ynyl, 2-oxooctadecyl, 18-cyanooctadecyl, 2-methoxyeicosyl, 18-chlorooctadecyl, 18,18-dichlorooctadecyl, 18,18,18-trifluorooctadecyl, 18,18,18-trichlorooctadecyl, 17,17,18,18,18-pentachlorooctadecyl, 16,16,17,17,18,18,18-heptachlorooctadecyl and 16,16,17,17,18,18,18-heptafluorooctadecyl. The higher alkyl group substituted by halogen includes, in addition to those mentioned above, halogeno-higher alkyl groups represented by the formula:

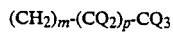

$(CH_2)_m$-$(CQ_2)_p$-$CQ_3$ wherein Q means halogen (preferably fluorine), m and p are independently an integer of 0 or more, and m+p is 7–21. The said halogeno-higher alkyl group includes $-(CH_2)_{11}-(CF_2)_7-CF_3$ and $-(CH_2)_6-(CF_2)_{11}-CF_3$.

The lower alkyl group represented by $R^2$ includes straight-chain or branched-chain alkyl groups having 1–5 carbon atoms, such as methyl, ethyl, propyl, butyl, pentyl, isopropyl, isobutyl, isopentyl, and sec-butyl. The said lower alkyl group may be substituted with lower alkanoyl having 2–4 carbon atoms, carboxyl, carboxylato, oxiranyl or halogen (e.g. fluorine). The said substituted lower alkyl group includes 2-oxopropyl, 2-oxobutyl, 3-oxobutyl, carboxymethyl, carboxylatomethyl, oxiranylmethyl, and 2,2,2-trifluoroethyl.

The lower alkanoyl group represented by $R^2$ includes alkanoyl groups having 2–4 carbon atoms, such as acetyl, propionyl and butyryl. The said lower alkanoyl group may be substituted with lower alkanoyl group having 2–4 carbon atoms, and the said substituted lower alkanoyl group includes acetoacetyl.

The lower alkylthiocarbamoyl group represented by $R^2$ includes thiocarbamoyl groups substituted with lower alkyl group having 1–4 carbon atoms, such as N-methylthiocarbamoyl, N-ethylthiocarbamoyl, N-propylthiocarbamoyl, and N-butylthiocarbamoyl.

The primary, secondary or amino group represented by $R^3$ includes groups represented by the formula:

wherein $R^4$ and $R^5$ are independently hydrogen or a lower alkyl group, or $R^4$ and $R^5$ taken together with the adjacent nitrogen atom, form a cyclic amino group.

The lower alkyl group represented by $R^4$ or $R^5$ includes alkyl groups having 1–5 carbon atoms, such as methyl, ethyl, propyl, butyl and pentyl, among which methyl group is preferable.

The cyclic amino group includes 5- or 6-membered cyclic amino group such as pyrrolidino, piperidino, piperazino, and morpholino, and these groups may have a substituent such as lower alkyl group having 1–4 carbon atoms (e.g. methyl, ethyl, propyl, butyl), hydroxy group, hydroxyethyl group, aminoethyl group, carbamoyl group, or ureido group.

The quaternary ammonium group represented by $R^3$ includes groups represented by the formula:

wherein $R^4$, $R^5$, and $R^6$ are independently hydrogen or a lower alkyl group, or

means a cyclic ammonium group.

The lower alkyl group represented by $R^4$, $R^5$, or $R^6$ includes alkyl groups having 1–5 carbon atoms (e.g.

methyl, ethyl, propyl, butyl, pentyl), among which methyl is preferable.

The cyclic ammonium group includes pyridinio, oxazolio, thiazolio, pyridazinio, quinolinio, isoquinolinio, 1-[lower($C_{1-4}$)alkyl]pyrrolidinio, 1-[lower($C_{1-4}$)alkyl]piperidinio, N-[lower($C_{1-4}$)alkyl]morpholinio, and 1-[lower($C_{1-4}$)alkyl]piperazinio, and these groups may be substituted with lower alkyl group having 1-4 carbons (e.g. methyl, ethyl, propyl, butyl), hydroxy group, hydroxyethyl group, aminoethyl group, carbamoyl group, or ureido group.

When $R^3$ is a primary, secondary or tertiary amino group, the compound (I) may form a pharmaceutically acceptable salt with an inorganic acid (e.g. hydrochloric acid, hydrobromic acid, hydroiodic acid, sulfuric acid) or an organic acid (e.g. acetic acid, lactic acid, tartaric acid, citric acid, methanesulfonic acid, ethanesulfonic acid, benzenesulfonic acid, toluenesulfonic acid).

When $R^3$ is a quaternary ammonium group, the compound (I) forms a pharmaceutically acceptable salt with an anion ($X^{31}$) of an inorganic acid (e.g. hydrochloric acid, hydrobromic acid, hydroiodic acid, sulfuric acid or of an organic acid (e.g. acetic acid, lactic acid, tartaric acid, citric acid, methanesulfonic acid, ethanesulfonic acid, benzenesulfonic acid, toluenesulfoni acid). Desirable anions include halogen ion (e.g. chlorine ion, bromine ion, iodine ion), anion of methanesulfonic acid, and anion of p-toluenesulfonic acid.

In the compound represented by the formula (I), the carbon atom at the 2-position of glycerol is an asymmetric center, and therefore there exist two stereoisomers having R-configuration and S-configuration. The individual stereoisomers, racemate and a mixture thereof are all included in the present invention.

The compound (I) of this invention can be produced, for example, by the following methods. (i) The compound in which $R^2$ is a lower alkyl group which may be substituted:

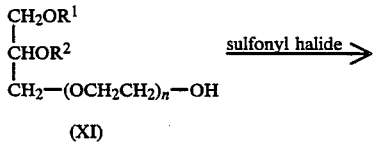

(XI)

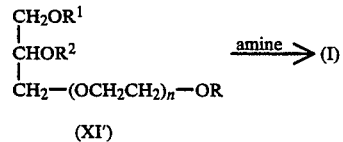

(XI')

wherein R is benzenesulfonyl, lower alkylbenzenesulfonyl or lower alkanesulfonyl, and the other symbols are the same as defined hereinbefore.

The compound (XI') can be obtained by the reaction of the compound (XI) with sulfonyl halide in a suitable anhydrous solvent (e.g. benzene, toluene, dichloromethane, chloroform, pyridine, or a mixture thereof) in the presence of a suitable acid binding agent (e.g. tertiary amines such as triethylamine and pyridine) at $-20°-+100°$ C., preferably at $-10°-+50°$ C. The sulfonyl halide used includes benzenesulfonyl halide (e.g. benzenesulfonyl chloride), lower($C_{1-4}$)alkylbenzenesulfonyl halide (e.g. toluenesulfonyl chloride), and lower($C_{1-4}$)alkanesulfonyl halide (e.g. methanesulfonyl chloride).

The compound (I) can be obtained by the reaction of the compound (XI') with an amine

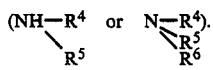

The said reaction is conducted in an excess of an amine or in a suitable solvent (e.g. water, methanol, ethanol, benzene, toluene, tetrahydrofuran, dimethylformamide, or a mixture thereof) at $-20-+150°$ C., preferably at $0°°-+80°$ C. If necessary, the reaction can be conducted in a sealed tube at ordinary temperature or by heating. Separation and purification of the compound (I) from the reaction mixture can be performed by known procedures such as distillation off of the solvent, extraction with a solvent, and silica gel column chromatography.

The starting compound (XI) for the synthesis can be produced by the following reactions.

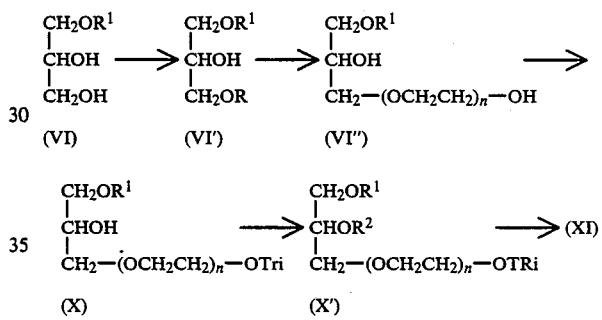

wherein Tri means trityl, and the other symbols are the same as defined hereinbefore.

The reaction (VI)→(VI') can be conducted similarly to the reaction (XI)→(XI').

The compound (VI") can be produced by the reaction of the compound (VI') with the compound represented by the formula: H—(OCH$_2$CH$_2$)$_n$—OH. The said reaction is conducted in a suitable solvent (e.g. benzene, toluene, hexane, dioxane, tetrahydrofuran) in the presence of a strong base (e.g. sodium hydroxide, potassium hydroxide, or an aqueous solution thereof), and preferably in the presence of a phase transfer catalyst (e.g. cetyltrimethylammonium chloride, benzyltrimethylammonium chloride) when the reaction is to be conducted in the presence of water, at $-20°-+150°$ C., preferably at $+20°-+100°$ C.

The reaction (VI")→(X) is tritylation of the compound (VI"), which can be conducted with use of trityl chloride a suitable solvent (benzene, toluene, dichloromethane, chloroform, pyridine or the like) in the presence a suitable acid-binding agent (e.g. tertiary amines such as triethylamine and pyridine) at $-20°-+150°$ C., preferably at $0°°-+120°$ C.

The reaction (X)→(X') is alkylation of the compound (X). The alkylating agent used includes alkyl halide [$R^2$—Y (Y means halogen)] and alkyl p-toluenesulfonate

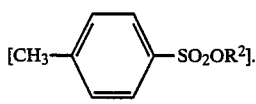

The said reaction is conducted in the presence of a base (e.g. sodium hydride, aqueous solution of sodium hydroxide) in a suitable solvent (benzene, toluene, tetrahydrofuran, dioxane, dimethylformamide, dimethylsulfoxide, or a mixture thereof), and preferably in the presence of a phase transfer catalyst(e.g. The same as described hereinbefore) when the reaction is to be conducted in the presence of water, at $-20°-+150°$ C., preferably at $0°°-+100°$ C. The compound (X') in which $R^2$ is a lower alkyl group substituted with a lower alkanoyl group can be obtained by the reaction of the compound (X) with a substituted epoxide (e.g. epibromohydrin, epichlorohydrin) in an appropriate solvent (e.g. hexane, benzene, toluene, tetrahydrofuran, dioxane, or a mixture thereof) in the presence of an acid-binding agent (e.g. sodium hydride), at $-20°-+100°$ C., preferably at $0°°-+50°$ C., followed by reaction in a suitable solvent (e.g. ether, tetrahydrofuran, dioxane, or a mixture thereof) with an epoxy-opening agent (e.g. lithium aluminum hydride) at $-30°-+50°$ C., preferably at $-20°-+30°$ C., and then with a suitable oxidant [e.g. chromium (VI) oxide-sulfuric acid, chromium (VI) oxide-acetic acid, chromium (IV) oxide-pyridine complex, dimethylsulfoxide-dicyclohexyldiimide, dimethylsulfoxide-pyridine-anhydrous sulfuric acid].

The compound (VI'') can also be obtained by the reaction of the compound represented by the formula:

wherein $R^1$ means the same as defined hereinbefore, with the compound represented by the formula: H—(OCH$_2$CH$_2$)$_n$—OH. The said reaction can be conducted similarly to the reaction (VI')→(VI''). The compound (VI''') can easily be obtained, for example by the reaction of alcohol (R$^1$—OH) with epichlorohydrin in the presence of alkali.

The compound (X) can also be obtained by the reaction of the compound (VI''') with the compound represented by the formula: H—(OCH$_2$CH$_2$)$_n$—OTri. The said reaction can be conducted similarly to the reaction (VI')→(VI'').

The compound (XI) can be obtained by reaction of the compound (X') with an acid (e.g. hydrochloric acid, trifluoroacetic acid, p-toluenesulfonic acid) in a suitable solvent (methanol, ethanol, dioxane, or a mixture thereof) containing water at 10° C. or higher or by heating under reflux, or with hydrogen chloride in chloroform at $-10°-+10°$ C., preferably at about 0° C., or in acetic acid containing water from $+30°$ C. or higher or by heating under reflux.

The compound (XI) can also be produced by the reactions described below.

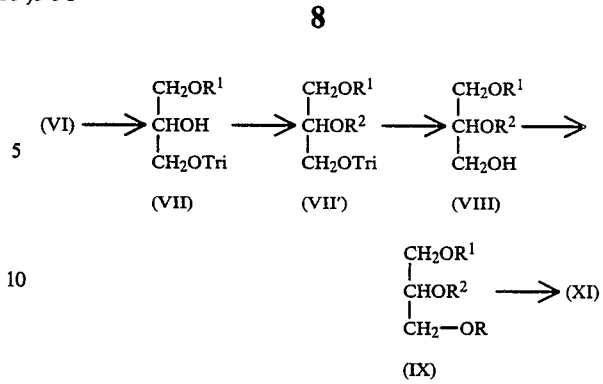

wherein the symbols are the same as defined hereinbefore.

The reactions (VI)→(VII), (VII)→(VII'), (VII')→(VIII), (VIII)→(IX), and (IX)→(XI) can be conducted similarly to the reactions (VI'')→(X), (X)→(X'), (X')→(XI), (VI)→(VI'), and (VI')→(VI''), respectively.

(ii) When $R^2$ is hydrogen or a lower alkanoyl group which may be substituted:

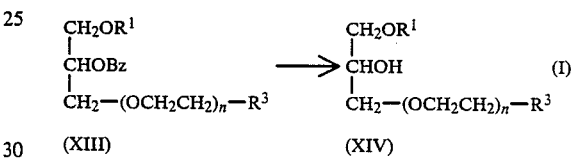

wherein Bz means benzyl, and the other symbols are the same as defined hereinbefore.

The compound (XIV) can be obtained by subjecting the compound (XIII) to catalytic reduction. The said catalytic reduction is conducted in an appropriate solvent (e.g. hydrous acetic acid, acetic acid, methanol, ethanol, or a mixture thereof) at $-20°-+150°$ C., preferably at $+10°-+100°$ C., in the presence of an appropriate catalyst (e.g. palladium-carbon, platinum).

The compound (I) can be obtained by subjecting the compound (XIV) to acylation. The acylating agent used includes acid anhydride, mixed acid anhydride, acid halide, and diketene. The reaction is conducted in a suitable solvent (benzene, toluene, pyridine, dichloromethane, chloroform, and the like) in the presence of a tertiary amine (e.g. triethylamine, pyridine) at $-20°-+150°$ C., preferably at $0°-+100°$ C. Separation and purification of the compound (I) from the reaction mixture can be conducted with the methods described hereinbefore.

The compound (XIII) can be obtained, for example, by the following reactions.

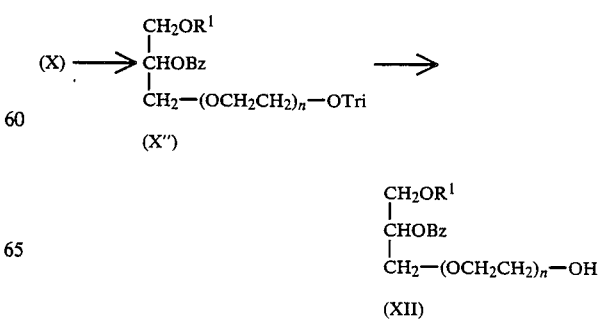

-continued

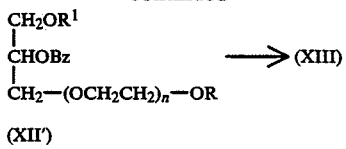
(XII')

wherein the symbols are the same as defined hereinbefore.

The reaction (X)→(X") can be conducted similarly to the reaction (X)→(X'), by using an alkylating agent such as benzyl chloride. The reactions (X")→(XII), (XII)→(XII'), and (XII')→(XIII) can be conducted similarly to the reactions (X')→(XI), (XI)→(XI'), and (XI')→(I), respectively.

The compound (XIV) can also be produced by the reactions described below:

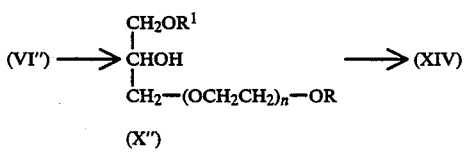

wherein the symbols are the same as defined hereinbefore.

The reactions (VI")→(X") and (X")→(XIV) can be conducted similarly to the reactions (XI)→(XI') and (XI')→(I), respectively.

The compound (XII) can also be synthesized by the following reactions:

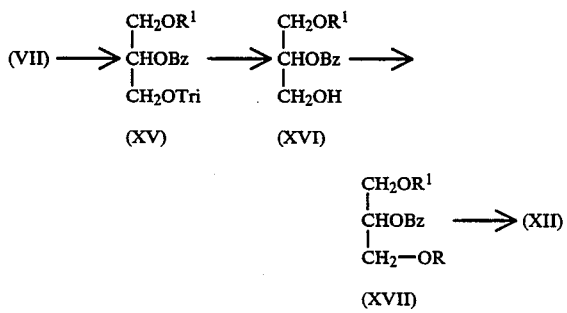

wherein the symbols are the same as defined hereinbefore.

The reactions (VII)→(XV), (XV)→(XVI), (XVI)→(XVII), and (XVII)→(XII) can be conducted similarly to the reactions (X)→(X"), (X')→(XI), (XI)→(XI'), and (VI')→(VI"), respectively. (iii) The compound in which $R^2$ is lower alkylthiocarbamoyl:

(XIV)→(I)

The compound (I) can be obtained by subjecting the compound (XIV) to thiocarbamoylation. The thiocarbamoylating agent used includes isothiocyanates such as methyl isothiocyanate. The reaction is conducted in a suitable solvent (pyridine, benzene, toluene, ether, dichloromethane, chloroform, or a mixture thereof) at 0°–+150° C., preferably at +50°–+120° C. (iv) The compound in which $R^2$ is a lower alkyl group which may be substituted:

(XIV)→(I)

The compound (I) can be obtained by subjecting the compound (XIV) to alkylation. The alkylating agent used includes alkyl halide [$R^2$—Y (Y means halogen)], and alkyl p-toluenesulfonate.

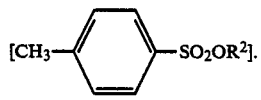

The said reaction is conducted the presence of a base (e.g. sodium hydroxide, sodium hydride) in a suitable organic solvent (e.g. benzene, toluene, tetrahydrofuran, dioxane, dimethylformamide, dimethylsulfoxide, or a mixture thereof), and preferably in the presence of a phase transfer catalyst (e.g. cetyltrimethylammonium chloride, benzyltrimethylammonium chloride) when the reaction is to be conducted in the presence of water, at −20°–+150° C., preferably at 0°–100° C.

The compounds obtained in the processes described above can be separated and purified by silica gel column chromatography, if necessary. Eluants include hexane-ethyl acetate mixture, and dichloromethane-ethyl acetate mixture.

When $R^3$ is a primary, secondary or tertiary amino group, the salt of the compound (I) may be obtained by the methods of production described above, but if necessary, also by addition of an inorganic or organic acid.

When $R^3$ is a quaternary ammonium group, the anion ($X^-$) can be exchanged with another anion by anion exchange resin, if necessary.

Representative methods of production of the compound (I) are described above, but the methods of production of the compound (I) should not be limited only to these.

EFFECT

The compounds (I) are found to have remarkable diminution of side effects (e.g. platelet-aggregating, blood pressure-lowering, vessel permeability-enhancing, tissue-impairing actions). Acute toxicities in mice are shown in Table 4 which indicates that the toxicities of the compounds are lower than those of the control agents Va and Vb.

The compounds (I) show increased efficacy and prolonged duration with respect to the main actions (e.g. antitumor action), and can be administered to cancer-carrying warm-blooded animals as safe antitumor agents. Schedule, route and dosage of administration can be selected according to the subject and symptoms to be treated; the dose for a mammal is usually about 0.1–150 mg/kg body weight, preferably about 2–50 mg/kg body weight, on the compound (I) basis. Frequency of administration of the pharmaceutical preparation of the compound is about 1–3 times a day, or at the intervals of 2–7 days. The preparation can also be administered by intravenous drip infusion over a long time to maintain the level of the compound in tissues at a required level over a long period. In parenteral administration of the, compound, combination with serum albumin or various globulins is expected to further improve the safety, for example by preventing tissue (local) impairment without affecting the efficacy.

The compounds (I) have PAF-inhibiting action, and therefore can be administered for prevention and treatment of PAF-mediated circulatory disorders (e.g. thrombosis, angina pectoris, cerebral infarction, endotoxin shock, anaphylactic shock) and allergy-related diseases (such as bronchial asthma). The dose of 0.2–20 mg/kg is preferable, and the other conditions of administration are the same as described above.

The compounds (I) and the salts thereof are excellent both in hydrophilic and in lipophilic properties, with low toxities, and therefore can be safely administered orally or parenterally to mammals as powders as they are or as a pharmaceutical composition in a suitable dosage form.

Pharmaceutical compositions used for administration contain an effective amount of the compound (I) or a salt thereof and a pharmaceutically acceptable carrier or excipient.

Injections for parenteral administration by this invention include sterilized aqueous or nonaqueous solutions, suspensions, and emulsions. Aqueous solutions and suspensions include distilled water for injection and physiological saline. Nonaqueous solutions and suspensions include Intralipid, propylene glycol, polyethylene glycol, vegetable oils such as olive oil, alcohols such as ethanol, and polysorbate 80. Such compositions may contain additionally supplements such as antiseptics, moistening agents, emulsifiers, and dispersants, and aqueous injections may contain supplements such as glucose, serum albumin, and serum (plasma) globulins. These preparations are sterilized by filtration through bacterial filter, by combination of a disinfectant, or by UV irradiation. Sterilized solid preparations are also produced, which are dissolved in sterilized water or sterilized solvent for injection before use. Tablets and capsules can be prepared in accordance with routine methods. To prepare these solid compositions, the compound (I) or a salt thereof is mixed with at least one inactive carrier or excipient such as lactose, mannitol, glucose hydroxypropylcellulose, microcrystalline cellulose and starch. The compositions may contain an additive other than inactive carrier or excipient, for example a lubricant such as magnesium stearate or a disintegrator such as calcium cellulose gluconate.

EXAMPLES

In the following, the present invention is illustrated in more detail by Working Examples and Reference Examples, but this invention should not be limited to these.

WORKING EXAMPLE 1

1-O-Octadecyl-3-O-[2-(2-trityloxyethoxy)ethyl]-glycerol 20.6 g (60 millimole) of batyl alcohol was dissolved in 70 ml of pyridine with heating, and stirred vigorously as soon as the container was immersed in an ice bath, to which was added dropwise rapidly 12.6 g (66 millimole) of p-toluenesulfonyl chloride dissolved in 200 ml of dichloromethane. Dichloromethane and pyridine were distilled off under reduced pressure, and the residue was partitioned between dilute hydrochloric acid and dichloromethane. The dichloromethane layer was washed with aqueous solution of sodium hydrogencarbonate and then dichloromethane was distilled off. The residue was dissolved in 50 ml of dioxane and 64 g of diethylene glycol, to which 3.6 g of 60% oily sodium hydride was added portionwise with stirring vigorously. After completion of the addition, the mixture was stirred at room temperature for 1 hour, followed by stirring at 90° C. for 13 hours. After cooling, the mixture was partitioned between ether and water. The aqueous layer was extracted twice with ether. The ether layers were combined and washed 5 times with water, and then ether was distilled off under reduced pressure. The residue was dissolved in 50 ml of pyridine, to which 16.7 g (60 millimole) of trityl chloride was added, and the resulting mixture was stirred at 40° C. for 15 hours.

Pyridine was distilled off under reduced pressure, and the residue was partitioned between dilute hydrochloric acid and dichloromethane. The dichloromethane layer was washed once with water, and dichloromethane was distilled off. The residue was purified by silica gel column chromatography (Merck Co., Art.7734, 350 g, Eluant: hexane-ethyl acetate=12:1–5:1), to give 16.2 g (40%) of the above-captioned compound.

IR(Neat)cm$^{-1}$: 3420, 1445, 1110, 1085, 705.

NMR(60 MHz, CDCl$_3$)δ: 0.90(3H), 1.27(32H), 2.70(1H), 3.17–3.83(15H), 7.17–7.60(15H).

WORKING EXAMPLE 2

1-O-Octadecyl-3-O-[2-[2-(2-trityloxyethoxy)ethoxy]ethyl]glycerol 10.3 g (30 millimole) of batyl alcohol, 6.1 g (32 millimole) of sodium p-toluenesulfonate, 50 ml of pyridine, 1.6 g (40 millimole) of 60% oily sodium hydride, 45 g (300 millimole) of triethylene glycol, and 8.4 g (30 millimole) of trityl chloride were treated by following a procedure similar to that of Working Example 1, to give 9.1 g (42%) of the above-captioned compound.

IR(Neat)cm$^{-1}$: 3430, 1490, 1465, 1445, 1110, 1085, 705.

NMR(60 MHz, CDCl$_3$)δ: 0.90(3H), 1.27(32H), 2.67(1H), 3.17–3.83(19H), 7.17–7.63(15H).

WORKING EXAMPLE 3

1-O-Octadecyl-3-O-[2-[2-(2-trityloxyethoxy)ethoxy]ethyl]glycerol 20.2 g (75 millimole) of stearyl alcohol, 21.4 g (230 millimole) of epichlorohydrin, 40 g of 50% sodium hydroxide, 1.2 g (3.75 millimole) of cetyltrimethylammonium chloride, and 200 ml of toluene were stirred for 14 hours on an oil bath at 60° C. After cooling, 300 ml of hexane and 15 g of anhydrous potassium carbonate were added and the resulting mixture was stirred sufficiently, followed by collection of the organic layer by decantation. The organic layer was subjected to evaporation under reduced pressure, and the residue was extracted with hexane. The insoluble material was filtrated off, and hexane was distilled off under reduced pressure. To the residue was added 0.8 g (20 millimole) of 60% oily sodium hydride with stirring vigorously at room temperature with 150 ml of dioxane and 100 ml of triethylene glycol, and the mixture was stirred at 80° C. for 15 hours after generation of hydrogen stopped. After cooling, dioxane was distilled off under reduced pressure, and the residue was partitioned between ether and water. The ether layer was washed 5 times with water, and ether was distilled off under reduced pressure. The residue was dissolved in 80 ml of pyridine, to which 22.3 g (80 millimole) of trityl chloride was added, and the resulting mixture was stirred at 40° C. for 15 hours. Pyridine was distilled off under reduced pressure, and the residue was partitioned between dilute hydrochloric acid and dichloromethane. The dichloromethane layer was washed once with water and dichloromethane was distilled off. The resulting residue was purified by silica gel column chromatography (Merck Co., Art.7734, 450 g, Eluant: hexane-ethyl acetate=12:1–5:1), to give 38.6 g (68%) of the above-captioned compound.

The IR and NMR values were identical with those described in Working Example 2.

WORKING EXAMPLE 4

1-O-Octadecyl-3-O-[2-(2-trityloxyethoxy)ethyl]-glycerol 27 g (100 millimole) of stearyl alcohol, 27.8 g (300 millimole) of epichlorohydrin, 56 g (700 millimole) of 50% sodium hydroxide, 1.6 g (5 millimole) of cetyltrimethylammonium chloride, 106 g (1 mole) of diethylene glycol, 1 g (25 millimole) of 60% oily sodium hydride, and 28 g (100 millimole) of trityl chloride were treated by following a procedure similar to that of Working Example 3, to give 43.9 g (65%) of the above-captioned compound.

The IR and NMR values were identical with those described in Working Example 1.

WORKING EXAMPLE 5

1-O-[2-(2-Hydroxyethoxy)ethyl]-2-O-methyl-3-O-octadecylglycerol 10.2 g (15 millimole) of 1-O-octadecyl-3-O-[2-(2-trityloxyethoxy)ethyl]glycerol obtained in Working Example 1, 5.6 g (30 millimole) of methyl p-toluenesulfonate, 8 g of 50% sodium hydroxide, and 96 mg (0.3 millimole) of cetyltrimethylammonium chloride were added to 40 ml of toluene, and the mixture was stirred at 40° C. for 15 hours. Toluene was distilled off under reduced pressure, and 50 ml of methanol was added to the residue. The mixture was stirred at 50° C. for 0.5 hours, and then methanol was distilled off under reduced pressure. The residue was partitioned between water and ether and the ether layer collected was washed with water, and then ether was distilled off. The residue was dissolved in 50 ml of methanol, 75 ml of dioxane and 20 ml of 2N hydrochloric acid, and the mixture was heated under reflux for 5 hours. The mixture was concentrated under reduced pressure, and the residue was partitioned between water and dichloromethane. The dichloromethane layer separated was washed with water, and dichloromethane was distilled off. The residue was purified by silica gel column chromatography (Merck Co., Art.7734, Eluant; hexane-ethyl acetate=4:1), to give 6 g (92%) of the above-captioned compound.

IR(Neat)cm$^{-1}$: 3425, 1110, 1065, 720.

NMR(90 MHz, CDCl$_3$)$\delta$: 0.90(3H), 1.27(32H), 2.50(1H), 3.40–3.80(18H).

WORKING EXAMPLE 6

1-O-[2-[2-(2-Hydroxyethoxy)ethoxy ]ethyl]-2-O-methyl-3-O-octadecylglycerol 4.47 g (10 millimole) of 1-O-[2-(2-hydroxyethoxy)ethyl]-2-O-methyl-3-O-octadecylglycerol obtained in Working Example 5 was dissolved in 15 ml of tetrahydrofuran, to which 2.9 g (15 millimole) of p-toluenesulfonyl chloride and 1.5 g (15 millimole) of triethylamine were added. The mixture was allowed to stand at room temperature for 100 hours, and then tetrahydrofuran was distilled off under reduced pressure. The residue was partitioned between dichloromethane and aqueous solution of sodium hydrogencarbonate, and after the dichloromethane layer was collected, dichloromethane was distilled off under reduced pressure. To the resulting residue were added 12.4 g (200 millimole) of ethylene glycol, 4 g (50 millimole) of 50% NaOH, 64 mg (0.2 millimole) of cetyltrimethylammonium chloride, and 40 ml of dioxane, and the mixture was stirred at 80° C. for 3 hours. Dioxane was distilled off under reduced pressure, and the residue was partitioned between ether and water. The organic layer was collected and ether was distilled off under reduced pressure. The residue was purified by silica gel column chromatography (Merck Co., Art.7734, 90 g, Eluant: hexane-ethyl acetate=2:1, hexane-ethyl acetate-acetone=3:1:1), to give 3.4 g (70%) of the above-captioned compound.

IR(Neat)cm$^{-1}$: 3440, 1110.

NMR(90 MHz, CDCl$_3$)$\delta$: 0.90(3H), 1.27(32H), 2.53(1H), 3.37–3.83(22H).

WORKING EXAMPLE 7

1-O-[2-[2-(2-Hydroxyethoxy)ethoxy]ethyl]-2-O-methyl-3-O-octadecylglycerol

To 10.8 g (15 millimole) of 1-O-octadecyl-3-O-[2-[2-(2-trityloxyethoxy)ethoxy]ethyl]glycerol obtained in Working Example 3 were added 5.6 g (30 mM) of methyl p-toluenesulfonate, 8 g (100 mM) of 50% sodium hydroxide, and 96 mg (0.3 mM) of cetyltrimethylammonium chloride, and the mixture was treated by following a procedure similar to that of Working Example 6, to give 6.48 g (90%) of the above-captioned compound.

The IR and NMR values were identical with those described in Working Example 6.

WORKING EXAMPLE 8

2-[2-[2-Methoxy-3-(octadecyloxy)propyloxy]ethoxy]ethyltrimethylammonium chloride 3.58 g (8 millimole) of 1-O-[2-(2-hydroxyethoxy)ethyl]-2-O-methyl-3-O-octadecylglycerol was dissolved in 32 ml of dichloromethane, to which 1.68 g (8.8 millimole) of p-toluenesulfonyl chloride and 880 mg (8.8 millimole) of triethylamine were added, and the mixture was allowed to stand at room temperature for 80 hours. The mixture was washed with dilute hydrochloric acid and then with aqueous solution of sodium hydrogencarbonate, and dichloromethane was distilled off under reduced pressure. The residue was dissolved in 40 ml of tetrahydrofuran, to which 10 ml of 30% aqueous solution of trimethylamine was added, and the mixture was allowed to stand at room temperature for 100 hours. Under reduced pressure the mixture was concentrated to dryness, and the residue was partitioned between dichloromethane and dilute hydrochloric acid. The organic layer was collected and then dichloromethane was distilled off under reduced pressure. The residue was dissolved in methanol and passed through a column of 100 ml of Amberlite ® IRA-410 [Cl](Eluant: methanol). The solvent was distilled off under reduced pressure and the residue was solidified by addition of acetone, collected by filtration, and then dried, to give 2.94 g (70%) of the above-captioned compound.

IR(Nujol)cm$^{-1}$: 3370, 1110, 955, 720.

NMR(60 MHz, CDCl$_3$—CD$_3$OD)$\delta$: 0.90(3H), 1.27(32H), 3.27(9H), 3.43–4.03(18H).

Elemental analysis for C$_{29}$H$_{62}$NO$_4$Cl.H$_2$O

Calcd.: C, 62.17; H, 11.87; N, 2.50.

Found : C, 62.24; H, 12.00; N, 2.48.

WORKING EXAMPLE 9

2-[2-[2-[2-Methoxy-3-(octadecyloxy)propyloxy]ethoxy]ethoxy]ethyltrimethylammonium chloride 2.1 g (4.4 mM) of 1-O-[2-[2-(2-hydroxyethoxy)ethoxy]ethyl]-2-O-methyl-3-O-octadecylglycerol, 1.15 g (6 mM) of methyl p-toluenesulfonate, 0.6 g (6 mM) of triethylamine, 5 ml of 30% aqueous solution of trimethylamine, and 100 ml of Amberlite ® IRA-410 [Cl] were treated by following a procedure similar to that described in Working Example 8, to give 2.42 g (95%) of the above-captioned compound.

IR(CHCl$_3$)cm$^{-1}$: 3310, 1235, 1110, 1095, 950.
NMR(90 MHz, CDCl$_3$)δ: 0.87(3H), 2.23(32H), 3.37–3.70(27H), 4.00(4H).
Elemental analysis for C$_{31}$H$_{66}$NO$_5$Cl.½H$_2$O
Calcd: C, 64.49; H, 11.70; N, 2.43.
Found : C, 64.43; H, 11.73; N, 2.25.

WORKING EXAMPLE 10

2-O-Benzyl-1-O-[2-(2-hydroxyethoxy)ethyl]-3-O-octadecylglycerol

To 6.5 g (9.6 millimole) of 1-O-octadecyl-3-O-[2-(2-trityloxyethoxy)ethyl]glycerol synthesized in Working Example 1 were added 2.3 g (18 millimole) of benzyl chloride, 4 g (50 millimole) of 50% sodium hydroxide, and 160 mg (0.5 millimole) of cetyltrimethylammonium chloride, and the mixture was stirred at 70° C. for 18 hours. After cooling, hexane was added and the organic layer was collected by decantation. Hexane was distilled off under reduced pressure, and to the residue 50 ml of dioxane, 8 ml of 2N hydrochloric acid and 20 ml of methanol were added, and then the resulting mixture was stirred at 75° C. for 4 hours. After addition of 50 ml of water, the organic solvent was distilled off under reduced pressure, and the residue was partitioned between dichloromethane and water. The organic layer was collected and dichloromethane was distilled off, and the residue was purified by silica gel column chromatography (Merck Co., Art.7734, 150 g, Eluant; hexane-ethyl acetate=6:1, hexane-ethyl acetate-acetone=6:1:1), to give 4.7 g (92%) of the above-mentioned compound.

IR(Neat)cm$^{-1}$: 3400, 1110, 1050.
NMR(90 MHz, CDCl$_3$)δ: 0.87(3H), 1.23(32H), 2.30(1H), 3.33–3.83(15H), 4.67(2H),7.27–7.47(5H).

WORKING EXAMPLE 11

2-[2-[2-Hydroxy-3-(octadecyloxy)propyloxy]ethoxy]ethyltrimethylammonium chloride 4.7 g (8.8 millimole) of 2-O-benzyl-1-O-[2-(2-hydroxyethoxy)ethyl]-3-O-octadecylglycerol, 2.3 g (12 millimole) of p-toluenesulfonyl chloride, and 1.2 g (12 millimole) of triethylamine were dissolved in 20 ml of tetrahydrofuran, and the mixture was allowed to stand at room temperature for 90 hours. Tetrahydrofuran was distilled off under reduced pressure, and the residue was partitioned between water and dichloromethane, and then dichloromethane was distilled off. To the residue 60 ml of dioxane, 20 ml of ethanol, and 10 ml of 30% aqueous solution of trimethylamine were added, and the mixture was heated in a sealed stainless steel tube (250 ml) for 3.5 hours on an oil bath at 85° C. The mixture was concentrated to dryness under reduced pressure, and the residue was partitioned between dilute hydrochloric acid and dichloromethane. After the organic layer was collected, the aqueous layer was extracted with dichloromethane, and the dichloromethane layers were combined and subjected to concentration under reduced pressure. The residue was dissolved in methanol, and passed through a column of 100 ml of Amberlite ® IRA-410 [Cl]. After elution with the same solvent, methanol was distilled off. The residue was dissolved in a mixture of 100 ml of 70% acetic acid and 50 ml of methanol, and the resulting mixture was subjected to hydrogenolysis in the presence of 2 g of 10% palladium-carbon (50% wet) at room temperature under atmospheric pressure. The catalyst was filtrated off and the filtrate was concentrated to dryness under reduced pressure. The residue was extracted with a mixture of 100 ml of toluene and 10 ml of ethanol, and the insoluble material was filtrated off, and then the solvent was distilled off under reduced pressure.

The residue was solidified by addition of acetone, collected by filtration, and then dried, to give 3.8 g (85%) of the above-captioned compound.

IR(Nujol)cm$^{-1}$: 3330, 1130, 1110, 1070, 960.
NMR(90 MHz, CDCl$_3$—CD$_3$OD)δ: 0.87(3H), 1.23(32H), 3.23–3.57(15H), 3.60–3.70(6H), 3.83–4.07(3H).

WORKING EXAMPLE 12

2-[2-[2-(Acetoacetyloxy)-3-(octadecyloxy)propyloxy]ethoxy]ethyltrimethylammonium chloride 1.5 g (2.94 millimole) of 2-[2-[2-hydroxy-3-(octadecyloxy)propyloxy]ethoxy]ethyltrimethylammonium chloride was dissolved in 80 ml of pyridine, to which 2 ml of diketene was added, and the mixture was stirred at 45° C. for 5 minutes. 10 ml of ethanol was added thereto, and the mixture was concentrated to dryness under reduced pressure. The residue was purified by silica gel column chromatography (Merck Co., Art.7734, 38 g, Eluant; chloroform-methanol=4:1–2:1), to give 1.5 g (86%) of the above-captioned compound.

IR(chloroform)cm$^{-1}$: 3320, 1745, 1715, 1240, 1145,1110, 910.
NMR(90 MHz, CDCl$_3$)δ: 0.87(3H), 1.23(32H), 2.27(3H), 3.33–3.67(23H), 3.97(3H), 5.17(1H).
Elemental analysis for C$_{64}$NO$_6$Cl.4/5H$_2$O
Calcd.: C, 63.14; H, 10.86; N, 2.30.
Found : C, 63.23; H, 11.04; N, 2.29.

WORKING EXAMPLE 13

2-O-Benzyl-1-O-[2-[2-(2-hydroxyethoxy)ethoxy]ethyl]-3-O-octadecylglycerol 7.2 g (10 millimole) of 1-O-octadecyl-3-O-[2-[2-(2-trityloxyethoxy)ethoxy]ethyl]glycerol, 2.5 g (20 millimole) of benzyl chloride, 4 g (50 millimole) of 50% sodium hydroxide, 160 mg (0.5 millimole) of cetyltrimethylammonium chloride were treated by following a procedure similar to that described in Working Example 10, to give 5.1 g (88%) of the above-captioned compound.

IR(Neat)cm$^{-1}$: 3420, 1110, 1050.
NMR(90 MHz, CDCl$_3$)δ: 0.87(3H), 1.23(32H), 2.37(1H), 3.33–3.80(19H), 4.67(2H), 7.23–7.43(5H).

WORKING EXAMPLE 14

2-[2-[2-[2-Hydroxy-3-(octadecyloxy)propyloxy]ethoxy]ethoxy]ethyltrimethylammonium chloride 5.1 g (8.8 millimole) of 2-O-benzyl-1-O -[2-[2-(2-hydroxyethoxy)ethoxy]ethyl]-3-O-octadecylglycerol, 2.3 g (12 millimole) of methyl p-toluenesulfonate, 1.2 g (12 millimole) of triethylamine, 10 ml of 30% aqueous solution of trimethylamine, 100 ml of Amberlite ® IRA-410 [Cl], and 2 g of 10% palladium-carbon (50% wet) were treated by following a procedure similar to that of Working Example 11, to give 4.3 g (88%) of the above-captioned compound.

IR(Nujol)cm$^{-1}$: 3340, 1130, 1110, 1070, 960.
NMR(90 MHz, CDCl$_3$—CD$_3$OD)δ: 0.87(3H), 1.23(32H), 3.23–3.57(15H), 3.60–3.70(10H), 3.83–4.07(3H).

WORKING EXAMPLE 15

2-[2-[2-[2-(Acetoacetyloxy)-3-(octadecyloxy)propyloxy]ethoxy]ethoxy]ethyltrimethylammonium chloride 1.7 g (3 millimole) of 2-[2-[2-[2-hydroxy-3-(octadecyloxy)propyloxy]ethoxy]ethoxy]ethyltrimethylammonium chloride and 2 ml of diketene were treated by following a procedure similar to that of Working Example 12, to give 1.7 g (85%) of the above-captioned compound.

IR(CHCl$_3$)cm$^{-1}$: 3325, 1745, 1715, 1240, 1150, 1110, 905.

NMR(90 MHz, CDCl$_3$)δ: 0.87(3H), 1.23(32H), 2.10(2H), 2.27(3H), 3.33–3.67(27H), 3.97(3H), 5.17(1H).

Elemental analysis for C$_{34}$H$_{68}$NO$_7$Cl.H$_2$O
Calcd.: C, 62.22; H, 10.75; N, 2.13.
Found : C, 62.01; H, 10.83; N, 2.37.

WORKING EXAMPLE 16

12-Cyclohexyldodecyl bromide

To 98 g (0.30 mole) of 1,12-dibromododecane in 300 ml of anhydrous tetrahydrofuran (THF), cyclohexyl magnesium bromide (0.30 mole) in 300 ml of THF was added dropwise at 10°–15° C. over a period of 1.5 hours in the presence of 0.5 mole percent of dilithium tetrachlorocuprate (Li$_2$CuCl$_4$), and the mixture was stirred at room temperature overnight. To the reaction mixture 16 ml of 2N sulfuric acid was added until pH became about 2, and about 500 ml of ethyl acetate was added. The insoluble material was filtrated off, and the filtrate was washed with water, saturated aqueous solution of sodium hydrogencarbonate, and water, successively, and dried over anhydrous magnesium sulfate. The organic layer was concentrated under reduced pressure, and the resulting oil was subjected to distillation under reduced pressure. The distillate having a boiling point of 166°–167° C. (0.3 mm Hg) was collected, to give 40 g (40%) of the above-captioned compound.

IR(Neat)cm$^{-1}$: 2920, 2850, 1460, 1440.

NMR(90 MHz, CDCl$_3$)δ: 1.26(26H), 1.45–1.93(7H), 3.45(2H).

WORKING EXAMPLE 17

1-O-(12-Cyclohexyl)dodecylglycerol

A mixture of 40.8 g (0.123 mole) of 12-cyclohexyldodecyl bromide, 22.7 g (0.172 mole) of 1,2-isopropylideneglycerol, 1.0 g of cetyltrimethylammonium chloride and 27.6 g (0.344 mole) of 50% aqueous solution of sodium hydroxide was stirred at 80° C. for 10 hours. Then to the reaction mixture was added 200 ml of hexane, and the resulting mixture was washed with water, and dried (MgSO$_4$), followed by evaporation of the solvent under reduced pressure. To the residue were added 200 ml of methanol and 4 ml of 6N hydrochloric acid, and the mixture was heated under reflux for 10 hours and then cooled. The precipitated colorless crystals were collected by filtration, washed with hexane, and dried, to give 10.1 g of the above-captioned compound. The mother liquid was further cooled, to give 20.8 g of the second crystals. Overall yield: 30.9 g (74%)

IR(KBr)cm$^{-1}$: 3375, 2920, 2850, 1460, 1325, 1120, 1055, 935.

NMR(90 MHz, CDCl$_3$)δ: 1.25(26H), 1.47–1.74(7H), 2.50(1H), 2.85(1H), 3.37–3.80(6H), 3.85(1H).

WORKING EXAMPLE 18

1-O-(12-Cyclohexyl)dodecyl-2-O-methylglycerol

A mixture of 23.5 g (68.6 millimole) of 1-O-(12-cyclohexyl)dodecylglycerol, 28.7 g (103 millimole) of trityl chloride, 13.7 g (137 millimole) of triethylamine and 200 ml of dichloromethane was stirred at room temperature for 2 days, and to the reaction mixture was added 10 ml of methanol. The resulting mixture was further stirred for 3 hours, and washed with water and dried (MgSO$_4$), followed by evaporation of the solvents, to give 52 g (quantitative) of crude 1-O-(12-cyclohexyl)dodecyl-3-O-tritylglycerol.

17 g (23 millimole) of the crude product was dissolved in 100 ml of tetrahydrofuran (THF), to which 1.84 g (46 millimole) of 60% sodium hydride was added. The mixture was stirred at room temperature for 1 hour, and 4 ml of methyl iodide was added. After the mixture was stirred at room temperature overnight, 5 ml of methanol was added to the mixture, and the solvent was distilled off under reduced pressure. The residue was dissolved in 200 ml of hexane, and washed with water and then with 1N hydrochloric acid. After evaporation of hexane, 30 ml of 1N hydrochloric acid and 60 ml of dioxane were added and the reaction mixture was stirred at 80° C. for 10 hours. The reaction mixture was neutralized with sodium hydrogencarbonate, and 60 ml of ethyl acetate was added thereto, and then the solvent was distilled off after washing with water and drying (MgSO$_4$). The residue was subjected to silica gel (200 g) column chromatography, and eluted with dichloromethane-ethyl acetate (5:1), to give the above-captioned compound as colorless solid. Yield: 6.6 g (81%).

IR(KBr)cm$^{-1}$: 3450, 2925, 2850, 1465, 1445, 1120.

NMR(90 MHz, CDCl$_3$)δ: 1.24(26H), 1.47–1.77(7H), 2.15(1H), 3.36–3.80(7H), 3.45(3H).

WORKING EXAMPLE 19

2-O-Benzyl-1-O-(12-cyclohexyl)dodecylglycerol

A mixture of 35 g (4.6 millimole) of 1-O -(12-cyclohexyl)dodecyl-3-tritylglycerol prepared in Working Example 18, 8.7 g (69 millimole) of benzyl chloride, 0.5 g of cetyltrimethylammonium chloride, 7.4 g (92 millimole) of 50% aqueous solution of sodium hydroxide and 50 ml of THF was stirred at 60° C. overnight. To the reaction mixture were further added 7.4 g (92 millimole) of 50% sodium hydroxide and 8.7 g (69 millimole) of benzyl chloride, and the resulting mixture was stirred overnight. THF was distilled off from the reaction mixture, and 100 ml of hexane was added to the residue, and then hexane was distilled off after washing with water. To the residue were added 120 ml of dioxane and 60 ml of 1N hydrochloric acid, and the mixture was stirred at 80° C. for 5 hours and then cooled. After neutralization with sodium hydrogencarbonate, 100 ml of ethyl acetate was added. The organic layer was washed with water and dried (MgSO$_4$), followed by evaporation of the solvent. The residue was allowed to stand at room temperature overnight. To this residue a small volume of hexane was added and the precipitated trityl alcohol was filtrated off. The filtrate was subjected to silica gel (500 g) column chromatography, and eluted with hexane-ethyl acetate (9:1), to give the above-captioned compound as colorless oil. Yield: 9.0 g (45%).

IR(Neat)cm$^{-1}$: 3420, 2920, 2850, 1465, 1450, 1115, 1060, 735, 695.

NMR(90 MHz, CDCl$_3$)δ: 1.26(26H), 1.50–1.78(7H), 3.37–3.72(8H), 4.68(2H), 7.37(5H).

WORKING EXAMPLE 20

1-O-(12-Cyclohexyl)dodecyl-3-O-mesyl-2-O-methylglycerol

To a mixture of 1.70 g (4.78 millimole) of 1-O-(12-cyclohexyl)dodecyl-2-O-methylglycerol, 580 mg (5.74 millimole) of triethylamine and 10 ml of dichloromethane, 657 mg (5.74 millimole) of mesyl chloride was added dropwise under ice cooling. After stirring for 1 hour under ice cooling, the reaction mixture was washed with water, saturated solution of sodium hydrogencarbonate, and water, successively, and dried ($MgSO_4$), followed by evaporation of the solvent. The residue was subjected to silica gel (60 g) column chromatography, and eluted with hexane-ethyl acetate (5:1), to give the above-captioned compound as colorless solid. Yield: 1.93 g (97%).

IR(KBr)$cm^{-1}$: 2925, 2850, 1345, 1170, 1125, 986, 965, 860.

NMR(90 MHz, $CDCl_3$)δ: 1.27(26H), 1.50–1.83(7H), 3.05(3H), 3.38–3.70(5H), 3.48(3H), 4.17–4.50(2H).

WORKING EXAMPLE 21

2-O-Benzyl-1-O-(12-cyclohexyl)dodecyl-3-O-mesylglycerol

By following a procedure similar to that of Working Example 20, 5.3 g (quantitative) of the above-captioned compound was obtained as colorless oil from 4.5 g (10.4 millimole) of 2-O-benzyl-1-O-(12-cyclohexyl)dodecylglycerol.

IR(Neat)$cm^{-1}$: 2925, 2850, 1450, 1355, 1175, 1115, 990, 965, 820, 740, 695.

NMR(90 MHz, $CDCl_3$)δ: 1.27(26H), 1.45–1.75(7H), 2.97(3H), 3.41(2H), 3.51(2), 3.81(1H), 4.31(2H), 4.68(2H), 7.37(5H).

WORKING EXAMPLE 22

1-O-(12-Cyclohexyl)dodecyl-3-O-[2-(2-hydroxyethoxy)ethyl]-2-O-methylglycerol 2.03 g (19.2 millimole) of diethylene glycol was dissolved in 10 ml of dimethylsulfoxide (DMSO), to which 0.576 g (14.4 millimole) of 60% sodium hydride was added, and the mixture was stirred at 75° C. for 1 hour. The mixture was cooled to room temperature, to which 1.93 g (4.62 millimole) of 1-O-(12-cyclohexyl)dodecyl-3-O-mesyl-2-O-methylglycerol in 5 ml of DMSO was added, and the reaction mixture was stirred at 75° C. for 1 hour. After the reaction, 20 ml of ice water and 50 ml of hexane-ethyl acetate (1:1) mixture were added to the reaction mixture, and the upper layer was separated after shaking thoroughly. The aqueous layer was extracted with 20 ml of hexane-ethyl acetate (1:1), and the organic layers were combined, washed with water and dried ($MgSO_4$), followed by evaporation of the solvent. The residue was subjected to silica gel (60 g) column chromatography, and eluted with hexane-ethyl acetate (1:1), to give 1.0 g (49%) of the above-captioned compound as colorless oil.

IR(Neat)$cm^{-1}$: 3430, 2920, 2850, 1460, 1445, 1115.

NMR(90 MHz, $CDCl_3$)δ: 1.27(26H), 1.47–1.75(7H), 2.50(1H), 3.33–3.67(15H), 3.45(3H).

WORKING EXAMPLE 23

2-O-Benzyl-1-O-(12-cyclohexyl)dodecyl-3-O-[2-(2-hydroxyethoxy)ethyl]glycerol

By following a procedure similar to that of Working Example 22, 1.95 g (36%) of the above-captioned compound was obtained as colorless oil from 5.3 g (10.4 millimole) of 2-O-benzyl-1-O-(12-cyclohexyl)dodecyl-3-O-mesylglycerol.

IR(Neat)$cm^{-1}$: 3440, 2920, 2850, 1450, 1115, 735, 695.

NMR(90 MHz, $CDCl_3$)δ: 1.25(26H), 1.43–1.74(7H), 2.50(1H), 3.33–3.78(15H), 4.68(2H), 7.31(5H).

WORKING EXAMPLE 24

2-[2-[3-(12-Cyclohexyl)dodecyloxy-2-methoxypropyloxy]ethoxy]ethyltrimethylammonium chloride By following a procedure similar to that of Working Example 8, 814 mg (71%) of the above-captioned compound was obtained from 1.0 g (2.25 millimole) of 1-O-(12-cyclohexyl)dodecyl-3-O-[2-(2-hydroxyethoxy)ethyl]-2-O-methylglycerol, by using mesyl chloride and 20% solution of trimethylamine in toluene instead of p-toluenesulfonyl chloride and 30% aqueous solution of trimethylamine, respectively.

IR(KBr)$cm^{-1}$: 3440, 2920, 2855, 1625, 1470, 115, 960.

NMR(90 MHz, $CDCl_3$—$CD_3OD$)δ: 1.27(26H), 1.45–1.80(7H), 3.27(9H), 3.37–3.77(13H), 3.45(3H), 3.95(2H).

WORKING EXAMPLE 25

2-[2-[3-(12-Cyclohexyl)dodecyloxy-2-hydroxypropyloxy]ethoxy]ethyltrimethylammonium chloride By following a procedure similar to that of Working Example 11, 1.5 g (79%) of the above-captioned compound was obtained from 1.95 g (3.75 millimole) of 2-O-benzyl-1-O-(12-cyclohexyl)dodecyl-3-O-[2-(2-hydroxyethoxy)ethyl]glycerol by using mesyl chloride and 20% solution of trimethylamine in toluene instead of p-toluenesulfonyl chloride and 30% aqueous solution of trimethylamine, respectively.

IR(Neat)$cm^{-1}$: 3400, 2930, 2850, 1480, 1465, 1110, 960.

NMR(90 MHz, $CDCl_3$—$CD_3OD$)δ: 1.25(26H), 1.45–1.76(7H), 3.27(9H), 3.27–3.75(13H), 3.93(2H).

WORKING EXAMPLE 26

2-[2-[2-Acetoacetyloxy-3-(12-cyclohexyl)dodecyloxypropyloxy]ethoxy]ethyltrimethylammonium chloride By following a procedure similar to that of Working Example 12, 450 mg (64%) of the above-captioned compound was obtained from 600 mg (1.21 millimole) of 2-[2-[3-(12-cyclohexyl)dodecyloxy-2-hydroxypropyloxy]ethoxy]ethyltrimethylammonium chloride.

IR(KBr)$cm^{-1}$: 3420, 2920, 2855, 1745, 1720, 1665, 1480, 1360, 1260, 1150, 1120, 960.

NMR(90 MHz, $CDCl_3$—$CD_3OD$)δ: 1.25(26H), 1.43–1.80(7H), 2.25(3H), 3.25(9H), 3.33–3.73(15H), 3.90(2H), 5.17(1H).

WORKING EXAMPLE 27

2-O-(2,3-Epoxypropyl)-1-O-octadecyl-3-O-[2-(2trityloxyethoxy)ethyl]glycerol 13.5 g (20 millimole) of 1-O-octadecyloxy-3-O-[2-(2-trityloxyethoxy)ethyl]glycerol obtained in Working Example 1, and 4.9 g (36 millimole) of epibromohydrin were dissolved in 15 ml of hexane, and 1 g (25 millimole) of 60% oily sodium hydride was added portionwise with stirring at room temperature. The mixture was stirred at room temperature for 15 hours, and then water was added thereto for partition. The organic layer collected was concentrated under reduced pressure, and the residue was purified by silica gel column chromatography (Merck Co., Art.7734, 300 g, Eluant:

hexane-ethyl acetate=30:1:1–5:1:1), to give 11.5 g (79%) of the above-captioned compound.

IR(Neat)cm$^{-1}$: 1110, 1085, 705.

NMR(90 MHz, CDCl$_3$)δ: 0.90(3H), 1.27(32H), 2.53–2.83(2H), 3.03–3.23(1H), 3.27–3.87(15H), 7.20–7.63(15H).

WORKING EXAMPLE 28

1-O-[2-(2-Hydroxyethoxy)ethyl]-3-O-octadecyl-2-(2-oxopropyl)glycerol 7.3 g (10 millimole) of 2-O-(2,3-epoxypropyl)-1-O-octadecyl-3-O-[2-(2-trityloxyethoxy)ethyl]glycerol obtained in Working Example 27 was dissolved in 100 ml of tetrahydrofuran. This tetrahydrofuran solution was added dropwise to 380 mg (10 millimole) of lithium aluminum hydride in 50 ml of tetrahydrofuran with stirring at room temperature. After completion of the addition, the mixture was stirred at room temperature for 2 hours, and 2 ml of water in 20 ml of tetrahydrofuran was added thereto with stirring vigorously. After the resulting precipitates turned white, 200 ml of ether was added and the insoluble material was filtrated off. The solvent was distilled off, and the residue was dissolved in 40 ml of dichloromethane, to which 3.2 g (15 millimole) of pyridium chlorochromate was added, and then the mixture was stirred at room temperature for 30 minutes. 500 ml of ether was added and the insoluble material was filtrated off, followed by evaporation of the organic solvent. The residue was dissolved in 100 ml of tetrahydrofuran, and 5 ml of 2N hydrochloric acid was added thereto, and then the mixture was allowed to stand at room temperature for 3 days. After addition of 100 ml of water, tetrahydrofuran was distilled off under reduced pressure, and the residue was extracted with ether, followed by evaporation of ether.

The residue was purified by silica gel column chromatography (Merck Co., Art.7734, 200 g, Eluant: hexane-ethyl acetate-acetone=15:1:1–3:1:1), to give 2.2 g (45%) of the above-captioned compound.

IR(Neat)cm$^{-1}$: 3400, 1730, 1115.

NMR(90 MHz, CDCl$_3$)δ: 0.87(3H), 1.23(32H), 2.17(3H), 2.50(1H), 3.50–3.80(13H), 4.23(2H)

WORKING EXAMPLE 29

2-[2-[3-(Octadecyloxy)-2-(2-oxopropyloxy)propyloxy]ethoxy]ethyltrimethylammonium chloride 2 g (4.1 millimole) of 1-O-[2-(2-hydroxyethoxy)ethyl]-3-O-octadecyl-2-(2-oxopropyl)glycerol obtained in Working Example 28 was dissolved in 10 ml of tetrahydrofuran, to which 456 mg (4.5 millimole) of triethylamine and 860 mg (4.5 millimole) of p-toluenesulfonyl chloride were added, and the mixture was allowed to stand at room temperature for 100 hours. 5 ml of 30% aqueous solution of trimethylamine was added thereto, and the mixture was stirred at room temperature for 100 hours. The mixture was then concentrated to dryness under reduced pressure, and the residue was dissolved in methanol and passed through a column of 100 ml of Amberlite ® IRA-410 [Cl] (Eluant: methanol). After methanol was distilled off, the residue was purified by silica gel column chromatography (Merck Co., Art.7734, 50 g, Eluant: methanol), to give 958 mg (40%) of the above-captioned compound.

IR(Nujol)cm$^{-1}$: 3330, 1730, 1110.

NMR(90 MHz, CDCl$_3$—CD$_3$OD)δ: 0.87(3H), 1.23(32H), 2.17(3H), 3.23(9H), 3.33–4.03(15H), 4.57(2H).

Elemental analysis for C$_{31}$H$_{64}$ClNO$_5$·H$_2$O

Calcd.: C, 63.72; H, 11.39; N, 2.40.
Found: C, 63.58; H, 11.42; N, 2.43.

WORKING EXAMPLE 30

2-O-Benzyl-1-O-(16,16,17,17,18,18,18)-heptafluorooctadecyl-3-O-mesylglycerol

By following a procedure similar to that of Working Example 20, 3.19 g (quantitative) of the above-captioned compound was obtained as colorless oil from 2.80 g (5.0 millimole) of 2-O-benzyl-1-O-(16,16,17,17,8,18,18)-heptafluorooctadecylglycerol.

IR(Neat)cm$^{-1}$: 2925, 2850, 1450, 1355, 1175, 1115.

NMR(90 MHz, CDCl$_3$)δ: 1.17–1.50(24H), 1.53–1.77(2H), 1.92–2 32(2H), 2.98(3H), 3.42–3.80(5H), 4.32(2H), 4.68(2H), 7.37(5H).

WORKING EXAMPLE 31

2-O-Benzyl-1-O-(16,16,17,17,18,18,18)-heptafluorooctadecyl-3-O-[2-(2-hydroxyethoxy)ethyl]glycerol By following a procedure similar to that of Working Example 22, 1.30 g (40%) of the above-captioned compound was obtained as colorless oil from 3.19 g (5.0 millimole) of 2-O-benzyl-1-O-(16,16,17,17,18,18,18)-heptafluorooctadecyl-3-O-mesylglycerol.

IR(Neat)cm$^{-1}$: 3430, 2920, 2850, 1450, 1115.

NMR(90 MHz, CDCl$_3$)δ: 1.16–1.49(24H), 1.50–1.76(2H), 1.91–2.30(2H), 2.50(1H), 3.32–3.77(15H), 4.68(2H), 7.33(5H).

WORKING EXAMPLE 32

2-[2-[3-(16,16,17,17,18,18,18)-Heptafluorooctadecyloxy-2-hydroxypropyloxy]ethoxy]ethyltrimethylammonium chloride By following a procedure similar to that of Working Example 11, 0.95 g (75%) of the above-captioned compound was obtained from 1.30 g (2.0 millimole) of 2-O-benzyl-1-O-(1616,17,17,18,18,18)-heptafluorooctadecyl-3-O-[2-(2-hydroxyethoxy)ethyl]glycerol.

IR(KBr)cm$^{-1}$: 3400, 2925, 2855, 1465, 1110.

NMR(90 MHz, CDCl$_3$—CD$_3$OD)δ: 1.17–1.50(24H), 1.53–1.76(2H), 1.92–2.31(2H), 3.28(9H), 3.28–3.76(13H), 3.92(2H).

WORKING EXAMPLE 33

2-[2-[2-Acetoacetyloxy-3-(16,16,17,17,18,18,18)-heptafluorooctadecyloxypropyloxy]ethoxy]ethyltrimethylammonium chloride By following a procedure similar to that of Working Example 12, 720 mg (70%) of the above-captioned compound was obtained from 900 mg (1.42 millimole) of 2-[2-[3-(16,16,17,17,18,18,18)-heptafluorooctadecyloxy-2-hydroxypropyloxy]ethoxy]ethyltrimethylammonium chloride.

IR(KBr)cm$^{-1}$: 3420, 2920, 2855, 1745, 1725, 1665, 1480, 1260, 1150.

NMR(90 MHz, CDCl$_3$—CD$_3$OD)δ: 1.16–1.51(24H), 1.54–1.77(2H), 1.91–2.30(2H), 2.26(3H), 3.26(9H), 3.32–3.75(15H), 3.91(2H), 5.16(1H).

WORKING EXAMPLE 34

2-[2-[3-(12-Cyclohexyl)dodecyloxy-2-methoxypropyloxy]ethoxy]ethylpyridinium chloride 2.0 g (4.5 millimole) of 1-O-(12-cyclohexyl)-dodecyl-3-O-[2-(2-hydroxyethoxy)ethyl]-2-O-methylglycerol was dissolved in 20 ml of dichloromethane, to which 0.95 g (5.0 millimole) of p-toluenesulfonyl chloride and 505 mg (5.0 millimole) of triethylamine were added, and the mixture was stirred at room temperature for 3 days.

The reaction mixture was washed with water and then with saturated solution of sodium hydrogencarbonate, and dried over anhydrous magnesium sulfate, followed by evaporation of the solvent under reduced pressure. The residue was dissolved in 20 ml of pyridine, and the mixture was stirred at 60° C. for 3 days, followed by evaporation of pyridine under reduced pressure. The residue was subjected to silica gel (30 g) column chromatography, and eluted with chloroform-methanol-water (65:15:2). The desired fraction was concentrated to dryness. The residue was dissolved in methanol and then subjected to ion exchange chromatography on 30 ml of Amberlite ® IRA-410 [Cl], and eluted with methanol. The desired fraction was concentrated under reduced pressure, and acetone was added to the residue. The insoluble material was collected by filtration and dried, to give 1.46 g (60%) of the above-captioned compound.

IR(KBr)cm$^{-1}$: 3400, 2920, 2850, 1465, 1115, 960.

NMR(90 MHz, CDCl$_3$—CD$_3$OD)δ: 1.27(26H), 1.46–1.81(7H), 3.33–4.03(16H), 5.08(2H), 8.00(2H), 8.41(1H), 9.30(2H).

WORKING EXAMPLE 35

1-O-Tetradecyl-3-O-[2-(2-trityloxyethoxy]ethyl]-glycerol 21.4 g (100 millimole) of tetradecyl alcohol, 14 g (150 millimole) of epichlorohydrin, 48 g (600 millimole) of 50% sodium hydroxide, 1.6 g (5 millimole) of cetyltrimethylammonium chloride, 106 g (1 mole) of diethylene glycol, 1.2 g (30 millimole) of 60% oily sodium hydride and 28 g (100 millimole) of trityl chloride were treated by following a procedure similar to that of Working Example 3, to give 26 g (42%) of the above-captioned compound.

IR(Neat)cm$^{-1}$: 3440, 1450, 1110, 1085, 705.

NMR(90 MHz, CDCl$_3$)δ: 0.90(3H), 1.27(24H), 2.77(1H), 3.20–3.87(15H), 7.20–7.67(15H).

WORKING EXAMPLE 36

1-O-[2-(2-Hydroxyethoxy)ethyl]-2-O-methyl-3-O-tetradecylglycerol 18.6 g (30 millimole) of 1-O-tetradecyl-3-O-[2-(2-trityloxyethoxy)ethyl]glycerol, 6.1 g (33 millimole) of methyl p-toluenesulfonate, 8 g (100 millimole) of 50% sodium hydroxide, 192 mg (0.6 millimole) of cetyltrimethylammonium chloride and 20 ml of 2N hydrochloric acid were treated by following a procedure similar to that of Working Example 5, to give 10.4 g (89%) of the above-captioned compound.

IR(Neat)cm$^{-1}$: 3430, 1110, 1070.

NMR(90 MHz, CDCl$_3$)δ: 0.90(3H), 1.27(24H), 2.43(1H), 3.47–3.83(18H).

WORKING EXAMPLE 37

2-[2-[2-Methoxy-3-(tetradecyloxy)propyloxy]ethoxy]ethyltrimethylammonium chloride 3.9 g (10 millimole) of 1-O-[2-(2-hydroxyethoxy)ethyl]-2-O-methyl-3-O-tetradecylglycerol, 2.9 g (15 millimole) of p-toluenesulfonyl chloride, 1.5 g (15 millimole) of triethylamine, 10 ml of 30% aqueous trimethylamine and 100 ml of Amberlite ® IRA-410 [Cl]were treated by following a procedure similar to that of Working Example 8, to give 3.9 g (81%) of the above-captioned compound.

IR(Nujol)cm$^{-1}$: 3375, 1110, 960, 715.

NMR(90 MHz, CDCl$_3$-CD OD)δ: 0.90(3H), 1.27(24H), 3.23(9H), 3.40–4.03(18H).

Elemental analysis for C$_{25}$H$_{54}$NO$_4$Cl.H$_2$O
Calcd.: C, 61.76; H, 11.61; N, 2.88.
Found : C, 61.58; H, 11.80; N, 2.93.

WORKING EXAMPLE 38

2-O-Benzyl-1-O-hexadecyl-3-O-mesylglycerol

By following a procedure similar to that of Working Example 20, 4.84 g (quantitative) of the above-captioned compound was obtained as colorless oil from 4.06 g (10 millimole) of 2-O-benzyl-1-O-hexadecylglycerol.

IR(Neat)cm$^{-1}$: 2920, 2855, 1460, 1355, 1175, 1115, 965, 740, 695.

NMR (90 MHz, CDCl$_3$)δ: 0.88(3H), 1.27(28H), 2.98(3H), 3.42(2H), 3.52(2H), 3.81(1H), 4.32(2H), 4.69(2H), 7.37(5H).

WORKING EXAMPLE 39

2-O-Benzyl-1-O-hexadecyl-3-O-[2-(2-hydroxyethoxy)ethyl]glycerol

By following a procedure similar to that of Working Example 22, 1.98 g (40%) of the above-captioned compound was obtained as colorless oil from 4.84 g (10 millimole) of 2-O-benzyl-1-O-hexadecyl-3-O-mesylglycerol.

IR(Neat)cm$^{-1}$: 3430, 2920, 2850, 1450, 1115, 735, 695.

NMR(90 MHz, CDCl$_3$)δ: 0.89(3H), 1.27(28H), 2.51(1H), 3.33–3.77(15H), 4.67(2H), 7.32(5H).

WORKING EXAMPLE 40

2-[2-[3-(Hexadecyloxy)-2-hydroxypropyloxy]ethoxy]ethyltrimethylammonium chloride By following a procedure similar to that of Working Example 11, 1.60 g (80%) of the above-captioned compound was obtained from 1.73 g (3.5 millimole) of 2-O-benzyl-1-O-hexadecyl-3-O-[2-(2-hydroxyethoxy)ethyl]glycerol.

IR(KBr)cm$^{-1}$: 3330, 2920, 2850, 1460, 1130, 1110, 1070, 960.

NMR(90 MHz, CDCl$_3$—CD$_3$OD)δ: 0.87(3H), 1.25(28H), 3.24–3.58(15H), 3.60–3.71(6H), 3.83–4.08(3H).

WORKING EXAMPLE 41

2-[2-[2-(Acetoacetyloxy)-3-(hexadecyloxy)propyloxy]ethoxy]ethyltrimethylammonium chloride By following a procedure similar to that of Working Example 12, 0.86 g (70%) of the above-captioned compound was obtained from 1.14 g (2.0 millimole) of 2-[2-[3-(hexadecyloxy)-2-hydroxypropyloxy]ethoxy]ethyltrimethylammonium chloride.

IR(chloroform)cm$^{-1}$: 3330, 1745, 1715, 1240, 1150, 910.

NMR(90 MHz, CDCl$_3$)δ: 0.88(3H), 1.24(28H), 2.27(3H), 3.33–3.68(23H), 3.98(2H), 5.16(1H).

WORKING EXAMPLE 42

2-[2-[2-(Methylthiocarbamoyloxy)-3-(octadecyloxy)propyloxy]ethoxy]ethyltrimethylammonium chloride 1.02 g (2 millimole) of 2-[2-[2-hydroxy-3-(octadecyloxy)propyloxy]ethoxy]ethyltrimethylammonium chloride obtained in Working Example 11 was heated with 5 ml of pyridine and 4 g of methyl isothiocyanate on a bath at 105° C. for 15 hours, and then concentrated to dryness under reduced pressure.

The residue was dissolved in methanol and passed through a column of 100 ml of Amberlite ® IRA-410

[Cl], and eluted with the same solvent. Methanol was distilled off and the residue was purified by silica gel column chromatography (Merck Co., Art.7734, 75 g, Eluant: chloroform-methanol=9:1–4:1), to give 470 mg (40%) of the above-captioned compound.

IR(Nujol)cm$^{-1}$: 3390, 1630, 1550, 1210, 1120.

NMR(90 MHz, CDCl$_3$)δ: 0.87(3H), 1.27(32H), 2.00(2H), 1.90(0.9H), 3.07(2.1H), 3.33–3.83(21H), 3.93–4.13(2H), 7.27–7.43(1H).

WORKING EXAMPLE 43

2-[2-[3-(12-Cyclohexyl)dodecyloxy-2-N-methylthiocarbamoyloxypropyloxy]ethoxy]ethyltrimethylammonium chloride A mixture of 2.0 g (3.94 millimole) of 2-[2-[3-(12-cyclohexyl)dodecyloxy-2-hydroxypropyloxy]ethoxy]ethyltrimethylammonium chloride synthesized in Working Example 23, 7.5 g of methyl isothiocyanate and 12 ml of pyridine was stirred at 100° C. for 20 hours, and the reaction mixture was concentrated to dryness. The residue was subjected to silica gel (50 g) column chromatography, and eluted with chloroform-methanol (9:1). The desired fraction was concentrated to dryness, and the residue was dissolved in methanol and subjected to ion exchange chromatography on a column of Amberlite ® IRA-410 [Cl](40 ml). The eluate was concentrated to dryness, to give 740 mg of the above-captioned compound as colorless oil. Yield: 32%.

IR(Neat)cm$^{-1}$: 3350, 2920, 2850, 1640, 1540, 1460, 360, 1205, 1115, 1030.

NMR(90 MHz, CDCl$_3$)δ: 1.25(26H), 1.41–1.80(7H), 90–3.10(3H), 3.37–4.05(23H), 5.72(1H), 8.13(1H).

WORKING EXAMPLE 44

N-2-[2-[2-Hydroxy-3-(octadecyloxyl)propyloxy]ethoxy]ethyl-N-methylpyrrolidinium chloride 4.7 g (8.8 millimole) of 2-O-benzyl-1-O-[2-(2-hydroxyethoxy)ethyl]-3-O-octadecylglycerol obtained in Working Example 10, and 0.97 g (9.7 millimole) of triethylamine were dissolved in 20 ml of dichloromethane, to which 1.11 g (9.7 millimole) of mesyl chloride was added under ice cooling. The reaction mixture was stirred at room temperature for 1 hour; and washed with water, saturated solution of sodium hydrogencarbonate, and water, successively, and then dried over anhydrous magnesium sulfate. The solvent was distilled off and the residue was dissolved in 20 ml of toluene, to which 3.74 g (44 millimole) of N-methylpyrrolidine was added. The reaction mixture was stirred at 50° C. for 24 hours, and concentrated under reduced pressure. The residue was dissolved in methanol and subjected to chromatography on a column of 100 ml of Amberlite ® IRA-410 [Cl] and eluted with the same solvent. Methanol was distilled off under reduced pressure, and 100 ml of 70% acetic acid, 50 ml of methanol and 2 g of 10% palladium-carbon (50% wet) were added to the residue for hydrogenolysis at room temperature under ordinary pressure. After completion of the reaction, the catalyst was filtrated off, and the filtrate was concentrated under reduced pressure. The residue was subjected to silica gel (100 g) column chromatography, and eluted with chloroform-methanol (5:1). The desired fraction was concentrated under reduced pressure, to give 3.0 g (64%) of the above-captioned compound.

IR(Neat)cm$^{-1}$: 3330, 2920, 2850, 1140, 1110, 1070, 960.

NMR(90 MHz, CDCl$_3$—CD$_3$OD)δ: 0.87(3H), 1.23(32H), 2.07(4H), 3.17(3H), 3.30–3.70(16H), 3.80–4.00(3H).

WORKING EXAMPLE 45

N-2-[2-[2-(Acetoacetyloxy)-3-(octadecyloxy)propyloxy]ethoxy]ethyl-N-methylpyrrolidinium chloride 1.5 g (2.80 millimole) of N-2-[2-[2-hydroxy-3-(octadecyloxy)propyloxy]ethoxy]ethyl-N-methylpyrrolidinium chloride obtained in Working Example 44 was suspended in 30 ml of pyridine and 30 ml of dichloromethane, and the suspension was stirred with 2 ml of diketene at room temperature for 2 hours. The reaction mixture was concentrated under reduced pressure after addition of 10 ml of ethanol, and the residue was subjected to silica gel (30 g) column chromatography, and eluted with chloroform-methanol (3:1). The desired fraction was concentrated under reduced pressure, to give 1.5 g (86%) of the above-captioned compound.

IR(chloroform)cm$^{-1}$: 3320, 2920, 2850, 1745, 1715, 1240, 1150, 1110.

NMR(90 MHz, CDCl$_3$)δ: 0.87(3H), 1.23(32H), 2.13(4H), 2.27(3H), 3.23(3H), 3.33–3.66(18H), 3.90(2H), 5.17(1H)

WORKING EXAMPLE 46

3-Octadecyloxymethyl-10-trimethylammonio-2,5,8-trioxadecane carboxylate 1.5 g (2.94 millimole) of 2-[2-[2-hydroxy-3-(octadecyloxy)propyloxy]ethoxy]ethyltrimethylammonium chloride obtained in Working Example 11, 1.07 g (11 millimole) of monochloroacetic acid and 4 g (50 millimole) of 50% sodium hydroxide were stirred in 25 ml of dioxane at 50° C. for 40 hours. To the mixture was added 3 g (50 millimole) of acetic acid with stirring on an ice bath. The mixture was concentrated to dryness under reduced pressure, and the residue was shaken for partition with 100 ml of saline and 200 ml of dichloromethane containing a small volume of ethanol. The upper layer was extracted with dichloromethane, and the dichloromethane layers were combined and subjected to evaporation under reduced pressure. The residue was dissolved in methanol, and passed through a column of 100 ml of Amberlite ® IRA-410 [OH] (eluant: methanol). Methanol was distilled off under reduced pressure and the residue was dissolved in 90% tetrahydrofuran and purified by column chromatography on 30 g of Amberlite ® CG-50 [H] (eluant: 90% tetrahydrofuran), to give 610 mg (36%) of the above-captioned compound.

IR(Nujol)cm$^{-1}$: 1600, 1115.

NMR(90 MHz, CDCl$_3$—CD$_3$OD)δ: 0.83(3H), 1.20–1.67(32H), 3.13(9H), 3.40–3.97(15H), 4.30(2H).

WORKING EXAMPLE 47

2-[2-[2-(2,3-Epoxypropyloxy)-3-(octadecyloxy)-propyloxy]ethoxy]ethyltrimethylammonium chloride 1.29 g (2 millimole) of 2-[2-[2-hydroxy-3-(octadecyloxy)propyloxy]ethoxy]ethyltrimethylammonium chloride obtained in Working Example 11, 935 mg (10 millimole) of epichlorohydrin and 960 mg (12 millimole) of 50% sodium hydroxide were stirred in 10 ml of toluene on a bath at 50° C. for 16 hours. The toluene layer was concentrated under reduced pressure, and the residue was dissolved in methanol and passed through a column of 100 ml of Amberlite ® IRA-410 [Cl] (eluant: methanol). Methanol was distilled off.

The residue was purified by silica gel column chromatography (Merck Co., Art. 7734, 50 g, Eluant: chloroform-methanol=65:25), to give 590 mg (49%) of the above-captioned compound.

IR(Nujol)cm$^{-1}$: 1115, 955, 850.

NMR(90 MHz, CDCl$_3$)δ: 0.87(3H),1.23(32H), 2.53-2.67(1H), 2.80(1H), 3.03–3.23(1H), 3.07–3.73(24H), 3.80–4.07(2H).

REFERENCE EXAMPLE 1

12,12,13,13,14,14,15,15,16,16,17,17,18,18,19,19,19-Heptadecafluorononadecanol

The above-captioned compound was synthesized in accordance with the method described in T. Fuchikami et al. Tetrahedron Letters, 25, No. 3, 303–306 (1984) and the gazette of Japanese Unexamined Patent Publication (A) No. 181093/1985.

IR(Nujol)cm$^{-1}$: 3330, 1330, 1245, 1230. 1195, 1150.

NMR(90 MHz, CDCl$_3$)δ: 1.20–1.83(18H), 1.90–2.43(2H), 3.63(2H).

WORKING EXAMPLE 48

1,2-Epoxy-3-(12,12,13,13,14,14,15,15,16,16,17,17,18,18,19,19,19-heptadecafluorononadecyloxy)propane To a mixture of 5.5 g (9.3 millimole) of 12,12,13,13,14,14,15,15,16,16,17,17,18,18,19,19,19-heptadecafluorononadecyl alcohol obtained in Reference Example 1, 3.7 g (40 millimole) of epichlorohydrin and 160 mg (0.5 millimole) of cetyltrimethylammonium chloride, were added 20 ml of toluene and 4.8 g (60 millimole) of 50% sodium hydroxide, and the mixture was stirred in a 100 ml eggplant type flask on a bath at 60° C. for 13 hours.

After cooling, the mixture was extracted with 200 ml of hexane, and hexane was distilled off under reduced pressure. The residue was purified by silica gel column chromatography (Merck Co., Art. 7734, 60 g, Eluant: hexane-ether=10:1–4:1), to give 3.2 g (52%) of the above-captioned compound.

IR(Nujol)cm$^{-1}$: 1235, 1215, 1205, 1150, 1115, 1050.

NMR(90 MHz, CDCl$_3$)δ: 1.20–1.87(18H), 1.83–2.37(2H), 2.57(1H), 2.77(1H), 3.03–3.17(1H), 3.20–3.77(4H).

WORKING EXAMPLE 49

1-(12,12,13,13,14,14,15,15,16,16,17,17,18,18,19,19,19-Heptadecafluorononadecyl)-3-[2-[2-(2-methanesulfonyloxy)ethoxy]ethyl]glycerol 10.6 g (100 millimole) of diethylene glycol was dissolved in 24 ml of dioxane, in which 3.2 g (4.9 millimole) of 1,2-epoxy-3-(12,12,13,13,14,14,15,15,16,16,17,17,18,18,19,19,19-heptadecafluorononadecyloxy)propane obtained in Working Example 48 was dissolved. 64 mg (1.6 millimole) of 60% oily sodium hydride was added portionwise to the mixture with stirring vigorously on an oil bath at 110° C. After the mixture was stirred for 5 hours under the same conditions, dioxane was distilled off under reduced pressure. To the residue were added water and a mixture of etherhexane (2:1), and the resulting mixture was shaken for partition. The upper layer was collected, washed with water and evaporated under reduced pressure. The residue was dissolved in 20 ml of dichloromethane, to which 500 mg (5 millimole) of triethylamine and then 554 mg (4.9 millimole) of methanesulfonyl chloride were added with stirring on an ice bath. The mixture was stirred on an ice bath for 1.5 hours, and washed with dilute hydrochloric acid, and then with aqueous solution of sodium hydrogencarbonate. Dichloromethane was distilled off, and the residue was purified by silica gel column chromatography (Merck Co., Art. 7734, 150 g, Eluant: hexane-ethyl acetate-ether=10:1:1 2:1:1), to give 2.2 g (54%) of the above-captioned compound.

IR(Nujol)cm$^{-1}$: 3440, 1350, 1250, 1200, 1175, 1150, 1135, 1115, 1050, 1020, 975, 925.

NMR(90 MHz, CDCl$_3$—D$_2$O)δ: 1.10–1.77(18H), 1.90–2.40(2H), 3.07(3H), 3.37–4.07(13H), 4.33–4.43(2H).

WORKING EXAMPLE 50

2-[2-[2-Hydroxy-3-(12,12,13,13,14,14,15,15,16,16,17,17,18,18,19,19,19-heptadecafluorononadecyloxy)propyloxy]ethoxy]ethyltrimethylammonium methanesulfonate 2.2 g (2.6 millimole) of 1-(12,12,13,13,14,14,15,15,16,16,17,17,18,18,19,19,19-heptadecafluorononadecyl)3-[2-[2-(2-methanesulfonyloxy)ethoxy]ethyl]glycerol obtained in Working Example 49 was dissolved in a mixture consisting of 15 ml of dioxane, 10 ml of ethanol and 3 ml of 30% aqueous trimethylamine, and heated in a stainless steel tube having a volume of 100 ml at 65° C. for 13 hours. The reaction mixture was concentrated to dryness under reduced pressure, to give 2.3 g (96%) of the above-captioned compound.

IR(CHCl$_3$)cm$^{-1}$: 3350, 3000, 2925, 2860, 1470, 1240, 1150, 1135, 1110, 945.

NMR(90 MHz, CDCl$_3$—CD$_3$OD)δ: 1.15–1.77(18H), 1.90–2.37(2H), 2.73(3H), 3.27(9H), 3.33–4.07(15H).

WORKING EXAMPLE 51

2-[2-[2-Methoxy-3-(12,12,13,13,14,14,15,15,16,16,17,17,18,18,19,19,19-heptadecafluorononadecyloxy)propyloxy]ethoxy]ethyltrimethylammonium chloride 917 mg (1 millimole) of 2-[2-[2-hydroxy-3-(12,12,13,13,14,14,15,15,16,16,17,17,18,18,19,19,19-heptadecafluorononadecyloxy)propyloxy]ethoxy]ethyltrimethyl ammonium methanesulfonate obtained in Working Example 50 was added to a mixture consisting of 5 ml of dioxane, 5 ml of toluene and 10 ml of tetrahydrofuran, to which 372 mg (2 millimole) of methyl p-toluenesulfonate and 800 mg (10 millimole) of 50% sodium hydroxide were added. The mixture was stirred at room temperature for 15 hours, and then 5 ml of methanol was added. The resulting mixture was stirred at room temperature further for 2.5 hours, and the solvent was distilled off under reduced pressure. To the residue were added dilute hydrochloric acid and a small volume of ethanol, and the mixture was extracted with dichloromethane. The solvent was distilled off under reduced pressure. The residue was dissolved in methanol, and passed through a column of 100 ml of Amberlite ® IRA-410 [Cl] (eluant: methanol), and the solvent was distilled off under reduced pressure. The residue was solidified by addition of acetone, cooled on an ice bath, collected by filtration, washed with a small volume of cold acetone, and dried, to give 87 mg (90%) of the above-captioned compound.

IR(CHCl$_3$)cm$^{-1}$: 2930, 2860, 1470, 1240, 1155, 1130, 1110, 960.

NMR(90 MHz, CDCl$_3$—CD$_3$OD)δ: 1.17–1.80(18H), 1.90–2.37(2H), 3.27(9H), 3.33–4.07(18H).

WORKING EXAMPLE 52

2-[2-[2-Acetoacetyloxy)-3-(12,12,13,13,14,14,15,15,16,16,17,17,18,18,19,19,19-heptadecafluorononadecyloxy)propyloxy]ethoxy]ethyltrimethylammonium chloride 917 mg (1 millimole) of 2-[2-[2-hydroxy-3-(12,12,13,13,14,14,15,15,16,16,17,17,18,18,19,19,19-heptadecafluorononadecyloxy)propyloxy]ethoxy]ethyltrimethylammonium methanesulfonate obtained in Working Example 50 was dissolved in methanol, and passed through a column of 100 ml of Amberlite® IRA-410 [Cl] (eluant: methanol), and the eluate was concentrated under reduced pressure.

The residue was dissolved in a mixture of 10 ml of pyridine and 10 ml of dichloromethane, to which 0.5 ml of diketene was added, and the resulting mixture was stirred at room temperature for 4 hours.

After addition of 5 ml of ethanol, the mixture was concentrated to dryness under reduced pressure, and the residue was purified by silica gel column chromatography (Merck Co., Art. 7734, 20 g, Eluant: chloroform-methanol=6:1–4:1), to give 744 mg (79%) of the above-captioned compound.

IR(CHCl$_3$)cm$^{-1}$: 2930, 2860, 1745, 1720, 1240, 1150, 1130, 1110, 960.

NMR(90 MHz, CDCl$_3$)$\delta$: 1.13–1.80(18H), 1.93–2.47(2H), 2.27(3H), 3.27–3.70(22H), 3.87–4.10(4H), 5.20(1H).

REFERENCE EXAMPLE 2

6-(Perfluorododecyl)hexanol

The above-captioned compound was synthesized in accordance with the method described in T. Fuchikami et al. Tetrahedron Letters, 25, No. 3, 303–306 (1984) and in the gazette of Japanese Unexamined Patent Publication (A) No. 181093/1985.

IR(Nujol)cm$^{-1}$: 3375, 1380, 1240, 1210, 1155, 1045.

NMR(90 MHz, CDCl$_3$)$\delta$: 1.25–1.90(10H), 1.93–2.40(2H), 3.63(2H).

WORKING EXAMPLE 53

1,2-Epoxy-3-[6-(perfluorododecyl)hexyloxy]propane 6.5 g (9 millimole) of 6-(perfluorododecyl)hexanol obtained in Reference Example 2, 3.7 g (40 millimole) of epichlorohydrin, 8 g (100 millimole) of 50% sodium hydroxide and 160 mg (0.5 millimole) of cetyltrimethylammonium chloride were treated by following a procedure similar to that of Working Example 48, to give 2.1 g (30%) of the above-captioned compound.

IR(Nujol)cm$^{-1}$: 1380, 1250, 1205, 1155, 1120, 1045.

NMR(90 MHz, CDCl$_3$)$\delta$: 1.20–1.87(10H), 1.90–2.40(2H), 2.50–2.67(1H), 2.73(1H), 3.03–3.23(1H), 3.27–3.77(4H).

WORKING EXAMPLE 54

1-O-[6-(Perfluorododecyl)hexyloxy]-3-O-[2-(2-trityloxyethoxy)ethyl]glycerol 2.1 g (2.7 millimole) of 1,2-epoxy-3-[6-(perfluorododecyl)hexyloxy]propane obtained in Working Example 53 was dissolved in a mixture of 55 ml of dioxane and 15 ml of diethylene glycol by heating at 100° C. With stirring vigorously at the same temperature, 100 mg (2.5 millimole) of 60% oily sodium hydride was added to the mixture and the resulting mixture was stirred under the same conditions for 15 hours.

The precipitates formed by cooling on an ice bath were collected by filtration, washed with ether, dried under reduced pressure, and added to a mixture of 50 ml of pyridine and 100 ml of dichloromethane. To the resulting mixture was added 3 g of trityl chloride, and the mixture was stirred at room temperature for 15 hours. The mixture was shaken with about 400 ml of a mixture of ether-hexane (3:1) and 100 ml of water for partition. The upper layer was collected, washed 3 times with 100 ml of water, and washed with 2N HCl to remove pyridine completely. The resulting solution was washed with aqueous solution of sodium hydrogencarbonate, and the solvent was distilled off under reduced pressure. The residue was purified by silica gel column chromatography (Merck Co., Ar. 7734, 100 g, Eluant: hexaneethyl acetate=5:1–2:1), to give 2.05 g (70%) of the above-captioned compound.

IR(Nujol)cm$^{-1}$: 3450, 3060, 3025, 1490, 1450, 1375, 1350, 1320, 1240, 1200, 1150, 1120, 1050, 1030, 1010.

NMR(90 MHz, CDCl$_3$)$\delta$: 1.20–2.40(21H), 3.17–4.10(15H), 7.20–7.52(15H).

WORKING EXAMPLE 55

1-O-[2-(2-Hydroxyethoxy)ethyl]-2-O-methyl-3-O-[6-(perfluorododecyl)hexyl]glycerol 2.05 g (1.88 millimole) of 1-O-[6-(perfluorododecyl)hexyl]-3-O-[2-[2-(2-trityloxyethoxy)ethyl]glycerol obtained in Working Example 54, 750 mg (4 millimole) of methyl p-toluenesulfonate, 32 mg (0.1 millimole) of cetyltrimethylammonium chloride and 400 mg (5 millimole) of 50% sodium hydroxide were treated by following a procedure similar to that of Working Example 5, to give 0.9 g (53%) of the above-captioned compound.

IR(Nujol)cm$^{-1}$: 3430, 1380, 1210, 1150, 1120, 1110, 1070, 1050.

NMR(90 MHz, CDCl$_3$—D$_2$O)$\delta$: 1.20–1.83(8H), 1.87–2.40(2H), 3.37–3.80(18H).

WORKING EXAMPLE 56

2-[2-[2-Methoxy-3-[6-(perfluorododecyl)hexyloxy]-propyloxy]ethoxy]ethyltrimethylammonium chloride 450 mg (0.462 millimole) of 1-O-[2-(2-hydroxyethoxy)ethyl]-2-O-methyl-3-O-[6-(perfluorododecyl)hexyl]-glycerol obtained in Working Example 55, and 1 ml of 30% aqueous trimethylamine were treated by following a procedure similar to that of Working Example 8, to give 185 mg (41%) of the above-captioned compound.

IR(Nujol)cm$^{-1}$: 3400, 1375, 1205, 1150, 1015.

NMR(90 MHz, CDCl$_3$—CD$_3$OD)$\delta$: 1.17–1.83(8H), 1.90–2.40(2H), 3.20–4.10(27H).

WORKING EXAMPLE 57

1-O-[2-(2-Hydroxyethoxy)ethyl]-3-O-(3,7,11,15-tetramethylhexadecyl)glycerol 14.9 g (50 millimole) of 3,7,11,15-tetramethylhexadecanol, 18.5 g (200 millimole) of epichlorohydrin and 106 g (1 mole) of diethylene glycol were treated by following a procedure similar to that of Working Example 4, and purification by silica gel column chromatography (Merck Co., Art. 7734, 400 g, Eluant: hexaneethyl acetate-acetone=3:1:1–2:1:1) was carried out, to give 15 g (65%) of the above-captioned compound.

IR(Neat)cm$^{-1}$: 3400, 2960, 2930, 2870, 1110.

NMR(90 MHz, CDCl$_3$)$\delta$: 0.77–1.70(39H), 2.27–2.43(2H), 3.40–3.80(14H).

WORKING EXAMPLE 58

2-[2-[2-Hydroxy-3-(3,7,11,15-tetramethylhexadecyloxy)propyloxy]ethoxy]ethyltrimethylammonium chloride 8.3 g (18 millimole) of 1-O-[2-(2-hydroxyethoxy)ethyl]-3-O-(3,7,11,15-tetramethylhexadecyl)glycerol obtained in Working Example 57 was dissolved in 60 ml of dichloromethane, to which 2.2 g (22 millimole) of triethylamine was added, and 2.3 g (20 millimole) of methanesulfonyl chloride was further added with stirring on an ice bath. Under the same conditions the mixture was stirred for 1 hour, and stirred further at room temperature for 2.5 hours.

Dichloromethane was distilled off under reduced pressure, and the residue was extracted with hexane. Hexane was distilled off, and the residue was dissolved in a mixture of 100 ml of dioxane and 15 ml of ethanol, to which 20 ml of 30% aqueous trimethylamine was added. The resulting mixture was allowed to stand at room temperature for 62 hours, and the mixture was concentrated to dryness under reduced pressure. The residue was dissolved in 200 ml of dichloromethane, to which were added saline containing 10 ml of 2N hydrochloric acid and a solution of dichloromethane containing a small volume of ethanol. The mixture was shaken for partition. The upper (water) layer separated was extracted with dichloromethane, and the dichloromethane layers collected were combined, and then dichloromethane was distilled off.

The residue was dissolved in methanol, and passed through a column of 100 ml of Amberlite ® IRA-410 [Cl](eluant: methanol). Methanol was distilled off under reduced pressure, and the residue was purified by silica gel column chromatography (Merck Co., Art. 7734, 130 g, Eluant: chloroform-methanol-water=65:25:4), to give 6.0 g (62%) of the above-captioned compound.

IR(Neat)cm$^{-1}$: 3380, 2955, 2930, 2870, 1110, 955.

NMR(90 MHz, CDCl$_3$—CD$_3$OD)δ: 0.77–1.70(39H), 3.23(9H), 3 40–4.10(15H).

WORKING EXAMPLE 59

2-[2-[2-Methoxy-3-(3,7,11,15-tetramethylhexadecyloxy)propyloxy]ethoxy]ethyltrimethylammonium chloride 1 08 g (2 millimole) of 2-[2-[2-hydroxy-3-(3,7,11,15-tetramethylhexadecyloxy)propyloxy]ethoxy]ethyltrimethylammonium chloride obtained in Working Example 58 and 1 g (5.4 millimole) of methyl p-toluenesulfonate were dissolved in 10 ml of tetrahydrofuran, to which 800 mg (10 millimole) of 50% sodium hydroxide was added, and then the mixture was stirred at room temperature for 20 hours. Tetrahydrofuran was distilled off under reduced pressure, and the residue was shaken with saline containing 10 ml of 2N hydrochloric acid and dichloromethane containing a small volume of ethanol for partition. The upper layer separated was extracted with dichloromethane, and the dichloromethane layers were combined, and then dichloromethane was distilled off under reduced pressure. The residue was dissolved in methanol and passed through a column of 100 ml of Amberlite ® IRA-410 [Cl](eluant: methanol). Methanol was distilled off to give 1.0 g (83%) of the above-captioned compound.

IR(Neat)cm$^{-1}$: 3400, 2955, 2925, 2870, 1110, 955.

NMR(90 MHz, CDCl$_3$—CD$_3$OD)δ: 0.77–1.70(39H), 3.23(9H), 3.43–3.73(16H), 3.83–4.07(2H).

WORKING EXAMPLE 60

2-[2-[2-Acetoacetyloxy-3-(3,7,11,15-tetramethylhexadecyloxy)propyloxy]ethoxy]ethyltrimethylammonium chloride 1.4 g (2.6 millimole) of 2-[2-[2-hydroxy-3-(3,7,11,15-tetramethylhexadecyloxy)propyloxy]ethoxy]ethyltrimethylammonium chloride obtained in Working Example 58, 1.5 ml of diketene and 30 ml of pyridine were treated by following a procedure similar to that of Working Example 12, to give 1.2 g (69%) of the above-captioned compound.

IR(Neat)cm$^{-1}$: 3395, 2955, 2930, 2870, 1745, 1715, 1150, 1120, 1045, 955.

NMR(90 MHz, CDCl$_3$)δ: 0.77–1.70(39H), 2.27(3H), 3 30–3.73(21H), 3.97(4H), 5.17(1H).

WORKING EXAMPLE 61

12-Cyclohexyldodecanol 57.8 g (165 millimole) of 2-[(12-bromododecyl)oxy]-tetrahydro-2H-pyran and 39.6 g (247 millimole) of cyclohexyl magnesium bromide were reacted by following a procedure similar to that of Working Example 16, to give crude 2-[(12-cyclohexyldodecyl)oxy]tetrahydro-2H-pyran. This crude product was dissolved in 450 ml of methanol, to which 4.5 g of Amberlist ® H-15 was added, and the resulting mixture was stirred at 45° C. for 2 hours. The resin was filtrated off, and the filtrate was concentrated to dryness under reduced pressure. The residue wa subjected to column chromatography on silica gel (1 kg), and eluted with hexane-ethyl acetate (6:1), to give the above-captioned compound as colorless solid.

Yield: 20.6 g (60%).

IR(KBr)cm$^{-1}$: 3370, 2890, 2840, 1620, 1460, 1450, 1350, 1050, 1030, 720.

NMR(90 MHz, CDCl$_3$)δ: 1.25(26H), 1.47–1.73(7H), 3.47–3.68(2H).

WORKING EXAMPLE 62

1-O-(12-Cyclohexyldodecyl)-3-O-[2-(2-trityloxyethoxy)ethyl]glycerol

A mixture of 26.5 g (99 millimole) of 12-cyclohexyldodecanol, 27.4 g (296 millimole) of epichlorohydrin, 52.6 g (658 millimole) of 50% aqueous solution of sodium hydroxide, 2.0 g of cetyltrimethylammonium chloride and 300 ml of toluene was stirred at 60° C. for 24 hours. The reaction mixture was washed with water, dried (anhydrous magnesium sulfate), and concentrated under reduced pressure. The residue was subjected to silica gel (550 g) column chromatography, and eluted with hexane-ethyl acetate (30:1), to give 1,2-epoxy-3-(12-cyclohexyldodecyloxy)propane as colorless oil.

Yield: 22.8 g (71%).

IR(Neat)cm$^{-1}$: 2920, 2850, 1450, 1340, 1250, 1110, 910, 840.

NMR(90 MHz, CDCl$_3$)δ: 1.10–1.75(32H), 2.58(1H). 3.13(1H), 3.27–3.77(4H) 2.78(1H),

Then 5.22 g (15 millimole) of diethylene glycol monotrityl ether was dissolved in 25 ml of dry dimethylformamide, to which 0.4 g (10 millimole) of sodium hydride (60% oily) was added, and the mixture was stirred at 60° C. for 1 hour. To this mixture was added 3.24 g (10 millimole) of the above epoxy derivative and the resulting mixture was stirred at 80° C. for 2 hours. The reaction mixture was concentrated under reduced pressure, and water was added to the residue. The mixture was extracted with hexane-ethyl acetate (1:1), and the organic layer was washed with water, dried and concentrated under reduced pressure. The residue was subjected to silica gel (100 g) column chromatography, and eluted with hexane-ethyl acetate (19:1), to give the above-captioned compound as colorless oil. Yield: 3.0 g (45%).

IR(Neat)cm$^{-1}$: 3430, 2920, 2850, 1450, 1085, 705.

NMR(90 MHz, CDCl$_3$)δ: 1.24(26H), 1.47–1.80(7H), 2.63(1H), 3.16–3.73(14H), 3.95(1H), 7.18–7.50(15H).

WORKING EXAMPLE 63

1-O-(12-Cyclohexyldodecyl)-2-O-(2,3-epoxypropyl)-3-O-[2-(2-trityloxyethoxy)ethyl]glycerol By following a procedure similar to that of Working Example 27, 5.0 g (yield: 77%) of the above-captioned compound was obtained from 6.0 g (8.93 millimole) of 1-O-(12-cyclohexyldodecyl)-3-O-[2-(2-trityloxyethoxy)ethl]glycerol obtained in Working Example 62.

IR(Neat)cm$^{-1}$: 2920, 2850, 1445, 1115, 1090, 705.

NMR(90 MHz, CDCl$_3$)δ: 1.25(26H), 1.40–1.73(7H), 2.55(1H), 2.70(1H), 3.30–3.92(18H), 7.20–7.50(15H).

WORKING EXAMPLE 64

1-O-(12-Cyclohexyldodecyl)-3-O-[2-(2-hydroxyethoxy)ethyl]-2-(2-oxopropyl)glycerol By following a procedure similar to that of Working Example 28, 1.67 g (yield: 50%) of the above-captioned compound was obtained from 5.0 g (6.87 millimole) of 1-O-(12-cyclohexyldodecyl)-2-O-(2,3-epoxypropyl)-3-O-[2-(2-trityloxyethoxy)ethyl]glycerol obtained in Working Example 63.

IR(Neat)cm$^{-1}$: 3440, 2920, 2850, 1720, 1460, 1445, 1355, 1115.

NMR(90 MHz, CDCl$_3$)δ: 1.27(26H), 1.43–1.80(7H), 302.16(3H), 2.60(1H), 3.33–3.80(15H), 4.23(2H).

WORKING EXAMPLE 65

2-[2-[3-(12-Cyclohexyldodecyloxy)-2-(2-oxopropyloxy)propyloxy]ethoxy]ethyltrimethylammonium chloride By following a procedure similar to that of Working Example 29, 0.90 g (yield: 59%) of the above-captioned compound was obtained as colorless wax from 1.31 g (2.70 millimole) of 1-O-(12-cyclohexyldodecyl)-3-O-[2-(2-hydroxyethoxy)ethyl]-2-(2-oxopropyl)glycerol obtained in Working Example 64.

IR(Neat)cm$^{-1}$: 3350, 2930, 2855, 1720, 1465, 1447, 355, 1110, 960.

NMR(90 MHz, CDCl$_3$)δ: 1.26(26H), 1.47–1.80(7H), 2.17(3H), 3.33–4.15(24H), 4.37(2H).

WORKING EXAMPLE 66

3-(12-Cyclohexyldodecyloxy)methyl-10-trimethylammonio-2,5,8-trioxadecane carboxylate By following a procedure similar to that of Working Example 46, 0.49 g (yield: 34%) of the above-captioned compound was obtained as colorless solid from 1.4 g (2.76 millimole) of 2-[2-[3-(12-cyclohexyldodecyloxy)-2-hydroxypropyloxy]ethoxy]ethyltrimethylammonium chloride obtained in Working Example 25.

IR(KBr)cm$^{-1}$: 3400, 2920, 2850, 1600, 1465, 1420, 1320, 1110, 960.

NMR(90 MHz, CDCl$_3$—CF$_3$COOH)δ: 1.25(26H), 1.63(7H), 3.18(9H), 3.60–3.90(15H), 4.28(2H).

WORKING EXAMPLE 67

1-O-(Hexadecyn-14-yl)-3-O-[2-(2-hydroxyethoxy)ethyl]-2-O-methylglycerol

By following a procedure similar to that of Working Example 62, 1,2-epoxy-3-(hexadecyn-14-yloxy)propane was obtained as colorless oil from 1.8 g (7.56 millimole) of 14-hexadecyn-1-ol. Yield 1.8 g (81%).

NMR(90 MHz, CDCl$_3$)δ: 1.20–1.67(22H), 1 75(3H), 2.16(2H), 2.60(1H), 2.77(1H), 3.13(1H), 3.23–3.76(4H).

Then 1.8 g (6.12 millimole) of this epoxy derivative was converted into crude 1-O-(hexadecyn-14-yl)-3-O-[2-(2-trityloxyethoxyethoxy)ethyl]glycerol by following the procedure described in Working Example 62. The crude product was dissolved in 20 ml of THF, to which 367 mg (9.18 millimole) of 60% sodium hydride was added, and the mixture was stirred at room temperature for 1 hour. To the reaction mixture was added dropwise 1.74 g (12.2 millimole) of methyl iodide in 4 ml of THF over a period of 20 minutes. The reaction mixture was stirred at room temperature overnight, to which was added 1 ml of methanol, and the mixture was concentrated under reduced pressure. The residue was extracted with hexane, and the hexane layer was washed with water, and then hexane was distilled off. To the residue were added 45 ml of dioxane, 30 ml of methanol and 12 ml of 2N hydrochloric acid, and the mixture was stirred at 70° C. for 1 hour. The reaction mixture was cooled, neutralized with saturated aqueous solution of sodium hydrogencarbonate, and concentrated under reduced pressure, and then the residue was extracted with ethyl acetate. The organic layer was washed with water and dried, and the solvent was distilled off. The residue was subjected to silica gel (50 g) column chromatography, and eluted with chloroform-methanol (9:1), to give the above-captioned compound as colorless oil.

Yield: 1.38 g (overall yield: 45%).

NMR(90 MHz, CDCl$_3$—CD$_3$OD)δ: 1.20–1.55(22H), 1.76(3H), 2.10(2H), 3.33–3.74(18H).

WORKING EXAMPLE 68

2-[2-[3-Hexadecyn-14-yloxy)-2-methoxypropyloxy]etoxy]ethyltrimethylammonium chloride 1.11 g (2.68 millimole) of 1-O-(hexadecyn-14-yl)-3-O-[2-(2-hydroxyethoxy)ethyl]-2-O-methylglycerol synthesized in Working Example 67 was treated by following a procedure similar to that of Working Example 24, to give the above-captioned compound as colorless wax. Yield: 1.0 g (76%).

IR(Neat)cm$^{-1}$: 3360, 2930, 2855, 1485, 1465, 1110, 960, 880.

NMR(90 MHz, CDCl$_3$—CD$_3$OD)δ: 1.20–1.60(22H), 1.75(3H), 2.10(2H), 3.28(9H), 3.30–3.77(16H), 3.90(2H).

WORKING EXAMPLE 69

2-[2-[3-(12-Cyclohexyldodecyloxy)-2-methoxypropyloxy]ethoxy]ethyldimethylamine 5.95 g (13.4 millimole) of 1-O-(12-cyclohexyldodecyl)-3-O-[2-(2-hydroxyethoxy)ethyl]-2-O-methylglycerol was dissolved in 30 ml of dichloromethane, to which 1.76 g (17.4 millimole) of triethylamine was added, and then 1.84 g (16.1 millimole) of methaneslfonyl chloride was added dropwise over a period of 30 minutes under ice cooling. The reaction mixture was stirred at the same temperature for 1 hour, washed with water, and dried over anhydrous magnesium sulfate. Dichloromethane was distilled off to give 7.0 g of colorless oil. 2.0 g of this product was dissolved in 10 ml of 20% dimethylamine in toluene, and stirred at room temperature overnight and then at 30° C. for 4 hours, and then concentrated under reduced pressure. To the residue were added 30 ml of dichloromethane and 10 ml of saturated aqueous solution of sodium hydrogencarbonate, and the mixture was shaken thoroughly. The organic layer was separated and dried over anhydrous magnesium sulfate, and the solvent was distilled off. The residue was subjected to silica gel (50 g) column chromatography, and eluted with chloroform-methanol (6:1), to give the above-captioned compound as colorless oil. Yield: 1.5 g (83%).

IR(Neat)cm$^{-1}$: 2920, 2855, 1465, 1120.

NMR(90 MHz, CDCl$_3$)δ: 0.80–1.35(26H), 1.45–1.80(7H), 2.30(6H), 2.56(2H), 3.33–3.67(16H).

WORKING EXAMPLE 70

2,2-Dimethyl-4-(2-methoxyeicosanyloxymethyl)-1,3-dioxolane 5.14 g (12.0 millimole) of 2,2-dimethyl-4-(2-hydroxyeicosanyloxymethyl)-1,3-dioxolane was dissolved in 40 ml of tetrahydrofuran, to which 0.72 g (18.0 millimole) of 60% oily sodium hydride was added. After the mixture was stirred at room temperature for 1 hour, a solution of 1.87 g (13.2 millimole) of methyl iodide in 10 ml of tetrahydrofuran was added dropwise. The reaction mixture was stirred at room temperature for 15 hours, extracted with ether, washed with water, and dried over anhydrous magnesium sulfate. After filtration, the filtrate was concentrated under reduced pressure, to give 5.30 g (quantitative) of a crude product of the above-captioned compound.

TLC Rf=0.39 (hexane-ethyl acetate=9:1).

NMR(90 MHz, CDCl$_3$)δ: 0.86(3H), 1.27(34H), 1.35(3H), 1.40(3H), 3.39(3H), 3.45–4.32(8H).

WORKING EXAMPLE 71

1-O-(2-Methoxyeicosanyl)glycerol 5.30 g (12.0 millimole) of 2,2-dimethyl-4-(2-methoxyeicosanyloxymethyl)-1,3-dioxolane obtained in Working Example 70 was dissolved in a mixture of 50 ml of 2N hydrochloric acid and 50 ml of tetrahydrofuran, and the mixture was stirred at room temperature for 17 hours. The mixture was extracted with ether, washed with water, and dried over anhydrous magnesium sulfate. After filtration, the filtrate was concentrated under reduced pressure. The residue was purified by silica gel column chromatography (Merck Co., Art. 7734, 100 g, Eluant: hexane-ethyl acetate=19:1–2:1), to give 3.54 g (73.4%) of the above-captioned compound.

TLC Rf=0.20 (hexane-ethyl acetate=1:1).

NMR(90 MHz, CDCl$_3$)δ: 0.87(3H), 1.27(34H), 3.39(3H), 3.23–3.67(7H), 3.80(1H).

WORKING EXAMPLE 72

1-O-(2-Methoxyeicosanyl)-3-O-tosylglycerol 3.50 g (8.69 millimole) of 1-(2-methoxyeicosanyl)-glycerol obtained in Working Example 71 was dissolved in 10 ml of pyridine, to which a solution of 1.82 g (9.56 millimole) of tosyl chloride in 30 ml of dichloromethane was added with stirring. The mixture was stirred at room temperature for 2 hours, and then stirred at 40° C. for 20 hours. After filtration, the filtrate was concentrated under reduced pressure. The residue was purified by silica gel column chromatography (Merck Co., Art. 7734, 70 g, Eluant: hexane-ethyl acetate=9:1–8:2), to give 3.25 g (67.1%) of the above-captioned compound.

TLC Rf=0.64 (hexane-ethyl acetate=1:1).

WORKING EXAMPLE 73

1,2-Epoxy-3-(2-methoxyeicosanyloxy)propane 1.17 g (2.09 millimole) of 1-(2-methoxyeicosanyl)-3-tosylglycerol obtained in Working Example 72 was dissolved in 20 ml of tetrahydrofuran, to which 2.35 g (20.9 millimole) of potassium tert-butoxide was added with stirring at room temperature, and the mixture was stirred at the same temperature for 20 minutes. To the reaction mixture was added water, and the resulting mixture was extracted with ethyl acetate. The extract was washed with water and dried over anhydrous magnesium sulfate. After filtration, the filtrate was concentrated under reduced pressure. The residue was purified by silica gel column chromatography (Merck Co., Art. 7734, 30 g, Eluant: hexane-ethyl acetate=9:1), to give 653 mg (yield: 81.1%) of the above-captioned compound.

TLC Rf=0.50 (hexane-ethyl acetate=4:1).

NMR(90 MHz, CDCl$_3$)δ: 0.87(3H), 1.27(34H), 2.59(1H), 2.77(1H), 3.15(1H), 3.30–3.47(8H).

WORKING EXAMPLE 74

1-O-(2-Methoxyeicosanyl)-3-O-[2-(2-hydroxy)ethoxy]ethylglycerol 5.47 g (51.5 millimole) of diethylene glycol was dissolved in 15 ml of dimethylformamide, to which 0.23 g (5.67 millimole) of 60% oily sodium hydride was added, and the mixture was stirred at 60° C. for 1 hour and then heated at 80° C. To this mixture a solution of 1.98 g (7.96 millimole) of 1,2-epoxy-3-(2-methoxyeicosanyloxy)propane obtained in Working Example 73 in 5 ml of dimethylformamide was added dropwise over a period of 20 minutes. The mixture was stirred at the same temperature for 5 hours, and the solvent was distilled off. Water was added to the residue, and the mixture was extracted with ethyl acetate. The extract was washed with water and dried over anhydrous magnesium sulfate. After filtration the filtrate was concentrated under reduced pressure. The residue was purified by silica gel column chromatography (Merck Co., Art. 7734, 40 g, Eluant: chloroform-methanol=40:1–30:1), to give 1.82 g (yield: 48.1%) of the above-captioned compound.

TLC Rf=0.55 (chloroform-methanol=8:1).

NMR(90 MHz,CDCl$_3$)δ: 0.87(3H), 1.26(34H), 1.92(1H), 2.67(1H), 3.10(1H), 3.47–3.70(15H), 3.97(1H).

WORKING EXAMPLE 75

1-O-(2-Methoxyeicosanyl)-3-O-[2-(2-trityloxy)ethoxy]ethylglycerol 1.80 g (3.67 millimole) of 1-(2-methoxyeicosanyl)-3-[2-(2-hydroxy)ethoxy]ethylglycerol obtained in Working Example 74 was dissolved in 20 ml of dichloromethane, to which 1.59 g (5.69 millimole) of trityl chloride was added and dissolved. 0.77 g (7.60 millimole) of triethylamine was added and the mixture was stirred at room temperature for 19 hours. The reaction mixture was washed with 1N hydrochloric acid, water, saturated aqueous solution of sodium hydrogencarbonate, and water, successively, and dried over anhydrous magnesium sulfate. After filtration, the filtrate was concentrated under reduced pressure. Petroleum ether was added to the residue and the resulting precipitates were filtrated off. The filtrate was concentrated under reduced pressure, to give a crude product of the above-captioned compound.

TLC Rf=0.64 (hexane-ethyl acetate=1:1).

WORKING EXAMPLE 76

1-O-(2-Methoxyeicosanyl)-2-O-methyl-3-O-[2-(2trityloxy)ethoxy]ethylglycerol

The crude product of 1-(2-methoxyeicosanyl)-3[2-(2-trityloxy)ethoxy]ethylglycerol obtained in Working Example 75 was dissolved in 30 ml of tetrahydrofuran, to which 455 mg (11.37 millimole) of 60% oily sodium hydride was added, and the mixture was stirred at 60° C. for 1 hour. After cooling to room temperature, a solution of 5.40 g (37.9 millimole) of methyl iodide in 5 ml of dimethylformamide was added dropwise to the mixture over a period of 25 minutes. The reaction mixture was stirred at room temperature for 30 minutes, and water was added to the mixture. The mixture was extracted with ether, and the extract was washed with water and dried over anhydrous magnesium sulfate. After filtration the filtrate was concentrated under reduced pressure. The residue was purified by silica gel column chromatography (Merck Co., Art. 7734, 75 g, Eluant: hexane-ethyl acetate=19:1–4:1), to give 1.78 g (yield: 65.0%) of the above-captioned compound.

TLC Rf=0.20 (hexane-ethyl acetate=4:1).

NMR(90 MHz,CDCl )$\delta$: 0.87(3H), 1.26(34H), 3.17–3.71(15H), 3.35(3H), 3.42(3H), 7.17–7.50(15H).

WORKING EXAMPLE 77

1-O-(2-Methoxyeicosanyl)-2-O-methyl-3-O-[2-(2-hydroxy)ethoxy]ethylglycerol 1.77 g (2.37 millimole) of 1-(2-methoxyeicosanyl)-2-methyl-3-[2-(2-trityloxy)ethoxy]ethylglycerol obtained in Working Example 76 was dissolved in a mixture of 45 ml of dioxane, 30 ml of methanol and 12 ml (24 millimole) of 2N HCl, and the mixture was stirred at 80° C. for 1 hour. The mixture was allowed to cool, and neutralized with 2.0 g (24 millimole) of sodium hydrogencarbonate. The mixture was concentrated under reduced pressure, and the residue was extracted with ether. The extract was washed with water, and dried over anhydrous magnesium sulfate. After filtration, the filtrate was concentrated under reduced pressure. The residue was purified by silica gel column chromatography (Merck Co., Art. 7734, 30 g, Eluant: chloroform-methanol=9:1), to give 1.13 g (yield: 94.7%) of the above-captioned compound.

TLC Rf=0.41 (chloroform-methanol=19:1).

NMR(90 MHz,CDCl$_3$)$\delta$: 0.87(3H), 1.26(34H), 1.38(2H), 1.95(1H), 2.60(1H), 3.39(3H), 3.48(3H), 3.33–3.75(12H).

WORKING EXAMPLE 78

1-O-(2-Methoxyeicosanyl)-2-O-methyl-3-[2-(2-mesyloxy)ethoxy]ethylglycerol 1.22 g (2.22 millimole) of 1-(2-methoxyeicosanyl)-2-methyl-3-[2-(2-hydroxy)ethoxy]ethylglycerol obtained in Working Example 77 was dissolved in 10 ml of dichloromethane, to which 1.14 g (11.10 millimole) of triethylamine was added, and then a solution prepared by dissolving 0.64 g (5.55 millimole) of mesyl chloride in 5 ml of dichloromethane with stirring at room temperature was added dropwise over a period of 10 minutes under cooling on a water bath. The mixture was stirred at room temperature for 10 minutes. The reaction mixture was washed with water, saturated aqueous solution of sodium hydrogencarbonate, and water, successively, and dried over anhydrous magnesium sulfate. After filtration, the filtrate was concentrated under reduced pressure, to give a crude product of the above-captioned compound.

WORKING EXAMPLE 79

2-[2-[2-Methoxy-3-(2-methoxyeicosanyloxy)propyloxy]ethoxy]ethyltrimethylammonium chloride The crude product of 1-(2-methoxyeicosanyl)-2-methyl-3-[2-(2-mesyloxy)ethoxy]ethylglycerol obtained in Working Example 78 was dissolved in 10 ml of 20% trimethylamine in toluene and the mixture was stirred at room temperature for 6 hours, and then stirred at 60° C. for 20 hours. The reaction mixture was concentrated under reduced pressure, and the residue was subjected to ion exchange chromatography on an Amberlite resin column (Organo Co., IRA-410 [Cl], 40 ml, Eluant: methanol), to give 1.14 g (yield: 88.4%) of the above-captioned compound.

TLC Rf=0.42 (chloroform-methanol-water=65:25:4).

NMR(90 MHz,CDCl$_3$)$\delta$: 0.87(3H), 1.27(32H), 1.40(4H), 3.28–3.62(15H), 3.38(3H), 3.43(3H), 3.49(9H).

IR(KBr)cm$^{-1}$: 3420, 2920, 2850, 1630, 1465, 1355, 1115, 955, 720.

WORKING EXAMPLE 80

1-O-(16,16,17,17,18,18,18-Heptafluorooctadecyl)-3-O-[2-(2-trityloxyethoxy)ethyl]glycerol 6 g (15 millimole) of 16,16,17,17,18,18,18-heptafluorooctadecanol was treated by following the procedure described in Working Example 4 and the product was purified by silica gel column chromatography (Merck Co., Art. 7734, 150 g, Eluant: hexane-ethyl acetate=4:1–3:1), to give 6.6 g (55%) of the above-captioned compound.

IR(Neat)cm$^{-1}$: 3480, 2930, 2860, 1450, 1355, 1225, 1200, 1170, 1120, 1110, 1090.

NMR(90 MHz,CDCl$_3$)$\delta$: 1.17–2.37(29H), 3.17–3.73(14H), 3.83–4.07(1H), 7.17–7.60(15H).

WORKING EXAMPLE 81

1-O-(16,16,17,17,18,18,18-Heptafluorooctadecyl)-2-O-methyl-3-O-[2-(2-hydroxyethoxy)ethyl]glycerol 6.6 g (8.2 millimole) of 1-O-(16,16,17,17,18,18,18-heptafluorooctadecyl)-3-O-[2-(2-trityloxyethoxy)ethyl]glycerol obtained in Working Example 80 was treated by following the procedure described in Working Example 5, and the product was purified by silica gel column chromatography (Merck Co., Art.7734, 100 g, Eluant: hexane-ethyl acetate=1:1–1:3), to give 3.85 g (82%) of the above-captioned compound.

IR(Neat)cm$^{-1}$: 3470, 2925, 2855, 1465, 1350, 1220, 1190, 1165, 1115, 1065.

NMR(90 MHz,CDCl$_3$)$\delta$: 1.20–2.40(28H), 2.22(1H), 3.37–3.80(18H).

WORKING EXAMPLE 82

2-[2-[3-(16,16,17,17,18,18,18-Heptafluorooctadecyloxy)-2-methoxypropyloxy]ethoxy]ethyltrimethylammonium chloride 1.4g (2.5 millimole) of 1-O-(16,16,17,17,18,18,18-heptafluorooctadecyl)-2-O-methyl-3-O-[2-(2-hydroxyethoxy)ethyl]glycerol was treated by following the procedure described in Working Example 8, and the product was purified by silica gel column chromatography (Merck Co., Art. 7734, 40 g, Eluant: chloroform-methanol-water=65:25:0–65:25:3), to give 940 mg (55%) of the above-captioned compound.

IR(Nujol)cm$^{-1}$: 3380, 1355, 1240, 1230, 1220, 1180, 1170, 1115.

NMR(90 MHz, CDCl$_3$)δ: 1.17–2.40(28H),3.33–3.73(23H), 3.97(4H).

WORKING EXAMPLE 83

N,N-Dimethyl-2-[2-[3-(16,16,17,17,18,18,18-heptafluorooctadecyloxy)-2-methoxypropyloxy]ethoxy]ethylamine 2.5 g (4.3 millimole) of 1-O-(16,16,17,17,18,18,18-heptafluorooctadecyl)-2-O-methyl-3-O-[2-(2-hydroxyethoxy)ethyl]glycerol obtained in Working Example 81 was treated by following the procedure described in Working Example 69, and the product was purified by silica gel column chromatography (Merck Co., Art. 7734, 100 g, Eluant: chloroform-methanol=8:1–4:1), to give 2.1 g (80%) of the above-captioned compound.

IR(Neat)cm$^{-1}$: 2920, 1860, 1465, 1350, 1220, 1195, 1165, 1115.

NMR(90 MHz, CDCl$_3$)δ: 1.13–1.83(26H), 1.90–2.40(2H), 2.27(6H), 2.50(2H), 3.37–3.70(16H).

WORKING EXAMPLE 84

N,N-Dimethyl-2-[2-[2-methoxy-3-(octadecyloxy)-propyloxy]ethoxy]ethylamine 4.6 g (10.3 millimole) of 1-O-[2-(2-hydroxyethoxy)ethyl]-2-O-methyl-3-O-octadecylglycerol obtained in Working Example 5 was treated by following the procedure described in Working Example 69, and the product was purified by silica gel column chromatography (Merck Co., Art. 7734, 150 g, Eluant: chloroform-methanol=10:1–3:1), to give 4.1 g (84%) of the above-captioned compound.

IR(Neat)cm$^{-1}$: 2925, 2860, 1465, 1120.

NMR(90 MHz, CDCl$_3$)δ: 0.87(3H), 1.23(32H), 2.27(6H), 2.50(2H), 3.33–3.70(16H).

WORKING EXAMPLE 85

2-O-Ethyl-1-O-[2-(2-hydroxyethoxy)ethyl]-3-O-octadecylglycerol 3.7 g (5.8 millimole) of 1-O-octadecyl-3-O-[2-(2-trityloxyethoxy)ethyl]glycerol and 1.5g (10 millimole) of diethyl sulfate were dissolved in 10 ml of dioxane, to which 96 mg (0.3 millimole) of cetyltrimethylammonium chloride and 2.4 g (30 millimole) of 50% sodium hydroxide were added, and the mixture was stirred at room temperature for 72 hours. Water and dichloromethane were added to the mixture and the resulting mixture was shaken for partition. Dichloromethane was distilled off and the residue was dissolved in a mixture of 20 ml of methanol and 25 ml of dioxane, to which 3 ml of concentrated hydrochloric acid was added. The mixture was stirred at 80° C. for 16 hours and then water was added to the mixture. The organic solvent was distilled off under reduced pressure, and water and ether were added to the residue. The resulting mixture was shaken for partition and ether was distilled off. The residue was purified by silica gel column chromatography (Merck Co., Art. 7734, 100 g, Eluant: hexane-ethyl acetate=3:1–1:1), to give 1.95 g (73%) of the above-captioned compound.

IR(Neat)cm$^{-1}$: 3450, 2920, 2855, 1465, 1110, 1070.

NMR(90 MHz, CDCl$_3$)δ: 0.87(3H), 1.17(3H), 1.27(32H), 2.50(1H), 3.33–3.80(17H).

WORKING EXAMPLE 86

N,N-Dimethyl-2-[2-[(2-ethoxy-3-octadecyloxy)-propyloxy]ethoxy]ethylamine 1.9 g (4.1 millimole) of 2-O-ethyl-1-O-[2-(2-hydroxyethoxy)ethyl]-3-O-octadecylglycerol obtained in Working Example 85 was treated by following the procedure described in Working Example 69, and the product was purified by silica gel column chromatography (Merck Co., Art. 7734, 60 g, Eluant: chloroform-methanol=10:1–3:1), to give 1.8 g (90%) of the above-captioned compound.

IR(Neat)cm$^{-1}$: 2925, 2855, 1465, 1115.

NMR(90 MHz, CDCl$_3$)δ: 0.87(3H), 1.17(3H), 1.27(32H), 2.27(6H), 2.50(2H), 3.37–3.77(15H).

WORKING EXAMPLE 87

1-O-[2-(2-Hydroxyethoxy)ethyl]-3-O-octadecyl-2-O-propylglycerol 3.8 g (6 millimole) of 1-O-octadecyl-3-O-[2-(2-trityloxyethoxy)ethyl]glycerol obtained in Working Example 4 was treated by following the procedure described in Working Example 85 and the product was purified by silica gel column chromatography (under same conditions as Working Example 85), to give 1.75 g (61%) of the above-captioned compound. p IR(Neat)cm$^{-1}$: 3460, 2920, 2855, 1465, 1110, 1070.

NMR(90 MHz, CDCl$_3$)δ: 0.87(3H), 0.90(3H), 1.27(32H), 1.53(2H), 2.50(1H), 3.33–3.80(17H).

WORKING EXAMPLE 88

N,N-Dimethyl-2-[2-[(3-octadecyloxy-2-propoxy)-propyloxy]ethoxy]ethylamine 1.75 g (3.7mM) of 1-O-[2-(2-hydroxyethoxyethyl]-3-O-octadecyl-2-O-propylglycerol obtained in Working Example 87 was treated by following the procedure described in Working Example 69, and the product was purified by silica gel column chromatography (Merck Co., Art. 7734, 60 g, Eluant: chloroform-methanol=10:1–3:1) to give 1.7 g (90%) of the above-captioned compound IR(Neat)cm$^{-1}$: 2920, 2855, 1465, 1115.

NMR(90 MHz, CDCl$_3$)δ: 0.87(3H), 0.90(3H), 1.53(2H), 2.27(6H), 2.50(2H), 3.33–3.70(15H).

WORKING EXAMPLE 89

2-O-Methanesulfonyl-1-O-octadecyl-3-O-[2-(2-trityloxyethoxy)ethyl]glycerol 3.4 g (5 millimole) of 1-O-octadecyl-3-O-[2-(2-trityloxyethoxy)ethyl]glycerol obtained in Working Example 4 was dissolved in 20 ml of dichloromethane, to which 650 mg (6.5 millimole) of trimethylamine was added. To the mixture 750 mg (6.5 millimole) of methanesulfonyl chloride was added with stirring on an ice bath, and the resulting mixture was stirred under the same conditions for 1.5 hours. To the mixture 100 ml of water and 200 ml of hexane were added, and the resulting mixture was shaken for partition. The upper layer was washed with water and the solvent was distilled off under reduced pressure. The residue was purified by silica gel column chromatography (Merck Co , Art. 7734, 100 g, Eluant: hexane-ethyl acetate=5:1–3:1) to give 2.7 g (71%) of the above-captioned compound.

IR(Neat)cm$^{-1}$: 2920, 2855, 1350, 1110.

NMR(90 MHz, CDCl$_3$)δ: 0.87(3H), 1.27(32H), 3.00(3H), 3.20(2H), 3.37(2H), 3.57–3.80(10H), 4.83(1H), 7.20–7.67(15H).

WORKING EXAMPLE 90

1-O-Octadecyl-2-O-(2,2,2-trifluoroethyl)-3-O-[2-(2-trityloxyethoxy)ethyl]glycerol 2.6 g (3.85 millimole) of 2-O-methanesulfonyl-1-O-octadecyl-3-O-[2-(2-trityloxyethoxy)ethyl]glycerol obtained in Working Example 89 and 2 g (20 millimole) of 2,2,2-trifluoroethanol were dissolved in 7 ml of toluene, to which 800 mg (10 millimole) of 50% sodium hydroxide and 64 mg (0.2 millimole) of cetyltrimethylammonium chloride were added, and the mixture was stirred at 80° C. for 120 hours. The mixture was cooled and extracted with hexane, and then hexane was distilled off under reduced pressure. The residue was purified by silica gel column chromatography (Merck Co., Art. 7734, 100 g, Eluant: hexane-ethyl acetate=5:1-3:1) to give 1.8 g (67%) of the above-captioned compound.

IR(Neat)cm$^{-1}$: 2975, 2860, 1495, 1465, 1450, 1280, 1160, 1120, 1090, 965.

NMR(90 MHz, CDCl$_3$)δ: 0.87(3H), 1.27(32H), 3.17-3.87(15H), 4.00(2H), 7.17-7.53(15H).

WORKING EXAMPLE 91

1-O-[2-(2-Hydroxyethoxy)ethyl]3-O-octadecyl-2-O-(2,2,2-trifluoroethyl)glycerol 1.8 g (2.6 millimole) of 3-O-octadecyl-2-O-(2,2,2-trifluoroethyl)-1-O-[2-(2-trityloxyethoxy)ethyl]glycerol obtained in Working Example 91 was dissolved in 15 ml of dioxane and 20 ml of methanol, to which 2 ml of concentrated hydrochloric acid was added, and the mixture was stirred at 75° C. for 1.5 hours. To the mixture 50 ml of water was added, and the organic solvent was distilled off under reduced pressure. The residue was purified by silica gel column chromatography (Merck Co., Art. 7734, 30 g, Eluant: hexane-ethyl acetate=3:1-1:1) to give 920 mg (80%) of the above-captioned compound.

IR(Neat)cm$^{-1}$: 3455, 1465, 1280, 1155, 1120, 1090.

NMR(90 MHz, CDCl$_3$)δ: 0.87(3H), 1.23(32H), 3.37-3.80(15H), 4.03(2H).

WORKING EXAMPLE 92

2-[2-[3-Octadecyloxy-2-(2,2,2-trifluoroethoxy)-propyloxy]ethoxy]ethyltrimethylammonium chloride 920 mg (2.1 millimole) of 1-O-[2-(2-hydroxyethoxy)ethyl]-3-O-octadecyl-2-O-(2,2,2-trifluoroethyl)glycerol obtained in Working Example 91 was treated by following the procedure described in Working Example 8, and the product was purified by silica gel column chromatography (Merck Co., Art. 7734, 25 g, Eluant: chloroform-methanol-water=65:25:4) to give 800 mg (65%) of the above-captioned compound.

IR(CHCl$_3$)cm$^{-1}$: 3330, 2925, 2855, 1465, 1275, 1160, 1115, 965.

NMR(90 MHz, CDCl$_3$—CD$_3$OD)δ: 0.87(3H), 1.27(32H), 3.30(9H), 3.33-3.93(15H), 4.03(2H).

WORKING EXAMPLE 93

2-[2-[(3-Octadecyloxy-2-propoxy)propyloxy]ethoxy]ethyltrimethylammonium chloride 2.1 g (5 millimole) of 2-[2-[2-hydroxy-3-(octadecyloxy)propyloxy]ethoxy]ethyltrimethylammonium chloride obtained in Working Example 11 and 2.55 g (15 millimole) of propyl iodide were dissolved in 12 ml of dichloromethane, to which 2.4 g (30 millimole) of 50% sodium hydroxide was added, and the mixture was stirred at room temperature for 15 hours. The mixture was acidified with 3 ml of concentrated hydrochloric acid, and then shaken with a mixture of dichloromethane-ethanol (20:1) and saline for partition. Dichloromethane was distilled off, and the residue was dissolved in methanol and passed through a column of 100 ml of IRA-410[Cl]for ion exchange (eluant: methanol). The solvent was distilled off under reduced pressure and the residue was purified by silica gel column chromatography (Merck Co., Art. ,7734, 100 g, Eluant: chloroform-methanol=9:1-3:1, chloroform-methanol-water=65:25:1-65:25:2) to give 845 mg (29%) of the above-captioned compound IR(CHCl)cm$^{-1}$: 3360, 2925, 2855, 1465, 1110.

NMR(90 MHz, CDCl)δ: 0.87(3H), 0.90(3H), 1.23(32H), 1.50(2H), 3.20-3.70(22H), 3.97(4H).

WORKING EXAMPLE 94

2-[2-[(2-Butoxy-3-octadecyloxy)propyloxy]ethoxy]ethyltrimethylammonium chloride

By following the procedure described in Working Example 93, 2.1 g (5 millimole) of 2-[2-[2-hydroxy-3-(octadecyloxy)propyloxy]ethoxy]ethyltrimethylammonium chloride and 1.8 g (10 millimole) of butyl iodide were treated, and the product was purified by silica gel column chromatography (Merck Co., Art 7734, 60 g, Eluant: chloroform-methanol=9:1-3:1) to give 900 mg (30%) of the above-captioned compound.

IR(CHCl$_3$)cm$^{-1}$: 3340, 2920, 2855, 1465, 1240, 1110, 950.

NMR(90 MHz, CDCl$_3$)δ: 0.87(3H), 0.90(3H), 1.23-1.70(36H), 3.30-3.70(22H), 3.97(4H).

WORKING EXAMPLE 95

1-O-Hexadecyloxy-3-O-[2-(2-trityloxy)ethyl]glycerol 24.2 g (0.1 mole) of cetyl alcohol was treated by following the procedure described in Working Example 4, to give 37 g (60%) of the above-captioned compound.

IR (Neat) cm$^{-1}$: 3430, 1445, 1110, 1085, 705.

NMR (90 MHz, CDCl$_3$)δ: 0.87(3H), 1.27(28H), 2.73(1H), 3.17-4.07(15H), 7.17-7.60(15H).

WORKING EXAMPLE 96

1-O-Hexadecyloxy-3-O-[2-(2-hydroxyethoxy)ethyl]-2-O-methylglycerol 6.1 g (10 millimole) of 1-O-hexadecyloxy-3-O-[2-(2-trityloxyethoxy)ethyl]glycerol obtained in Working Example 95 was treated by following the procedure described in Working Example 5, to give 3.45 g (77%) of the above-captioned compound.

IR (Neat) cm$^{-1}$: 3380, 2920, 2850, 1465, 1115, 1060.

NMR (90 MHz, CDCl$_3$—D$_2$O)δ: 0.87(3H), 1.27(28H), 3.37-3.80 (18H).

WORKING EXAMPLE 97

2-[2-[(3-Hexadecyloxy-2-methoxy)propyloxy]ethoxy]ethyltrimethylammonium chloride 1.2 g (2.68 millimole) of 1-O-hexadecyloxy-3-O-[2-(2-hydroxyethoxy)ethyl]-2-O-methylglycerol obtained in Working Example 96 was treated by following the procedure described in Working Example 8, to give 1.3 g (96%) of the above-captioned compound.

IR (CHCl$_3$) cm$^{-1}$: 3370, 2920, 2850, 1460, 1105, 950.

NMR (90 MHz, CDCl$_3$)δ: 0.87(3H), 1.27(28H), 3.33-3.73(23H), 3.97(4H).

WORKING EXAMPLE 98

Dimethyl-2-[2-[(3-hexadecyloxy-2-methoxy)propyloxy]ethoxy]ethylamine 1.0 g (2.2 millimole) of 1-O-hexadecyloxy-3-O-[2-(2-hydroxyethoxy)ethyl]-2-O-methylglycerol obtained in Working Example 96 was treated by following the procedure described in Working Example 69, to give 0.85 g (87%) of the above-captioned compound.

IR (Neat) cm$^{-1}$: 2920, 2855, 1465, 1115.
NMR (90 MHz, CDCl$_3$)δ: 0.87(3H), 1.27(28H), 2.30(6H), 2.53 (2H), 3.33–3.73(16H).

WORKING EXAMPLE 99

2-[2-[(3-Hexadecyloxy-2-methoxy)propyloxy]ethoxy]ethylpyridinium chloride 1.2 g (2.68 millimole) of 1-O-hexadecyloxy-3-O-[2-(2-hydroxyethoxy)ethyl]-2-O-methylglycerol obtained in Working Example 96 was treated by following the procedure described in Working Example 34, to give 1.03 g (73%) of the above-captioned compound.

IR (Neat) cm$^{-1}$: 3350, 2920, 2850, 1630, 1485, 1460, 1100.

NMR (90 MHz, CDCl$_3$)δ: 0.87(3H), 1.27(28H), 3.33–3.70(14H), 4.03(2H), 5.27(2H), 8.07(2H), 8.47(1H), 9.60(2H).

WORKING EXAMPLE 100

2-O-(2,3-Epoxypropyl)-1-O-hexadecyl-3-O-[2-(2-trityloxyethoxy)ethyl]glycerol 10.0 g (15.5 millimole) of 1-O-hexadecyloxy-3-O-[2-(2-trityloxyethoxy)ethyl]glycerol obtained in Working Example 95 was treated by following the procedure described in Working Example 27, to give 10.3 g (95%) of the above-captioned compound.

IR (Neat) cm$^{-1}$: 2925, 2855, 1445, 1115, 1090, 705.
NMR (90 MHz, CDCl$_3$)δ: 0.87(3H), 1.15–1.67(28H), 2.50–2.80 (2H), 3.33–3.95(18H), 7.20–7.50(15H).

WORKING EXAMPLE 101

1-O-Hexadecyl-3-O-[2-(2-hydroxyethoxy)ethyl]-2-O-(2-oxopropyl)glycerol 10.3 g (14.6 millimole) of 2-O-(2,3-epoxypropyl)-1-O-hexadecyl-3-O-[2-(2-trityloxyethoxy)ethyl]glycerol obtained in Working Example 100 was treated by following the procedure described in Working Example 28, to give 3.60 g (59%) of the above-captioned compound.

IR (Neat) cm$^{-1}$: 3420, 2920, 2855, 1720, 1465, 1115.
NMR (90 MHz, CDCl$_3$)δ: 0.86(3H), 1.27(26H), 1.53(2H), 2.15 (3H), 2.48(1H), 3.33–3.80(15H), 4.24(2H).

WORKING EXAMPLE 102

2-[2-[3-(Hexadecyloxy)-2-(2-oxopropyloxy)propyloxy]ethoxy]ethyltrimethylammonium chloride 1.50 g (3.26 millimole) of 1-O-hexadecyl-3-O-[2-(2-hydroxyethoxy)ethyl]-2-(2-oxopropyl)glycerol obtained in Working Example 101 was treated by following the procedure described in Working Example 29, to give 1.28 g (73%) of the above-captioned compound.

IR (Neat) cm$^{-1}$: 3400, 2920, 2855, 1720, 1465, 1115, 960.

NMR (90 MHz, CDCl$_3$)δ: 0.86(3H), 1.27(26H), 1.51(2H), 2.13 (3H), 3.31–3.62(24H), 4.27(2H).

WORKING EXAMPLE 103

Dimethyl-2-[2-[3-Hexadecyloxy-2-(2-oxopropyloxy)-propyloxy]ethoxy]ethylamine 1.50 g (3.26 millimole) of 1-O-hexadecyl-3-O-[2-(2-hydroxyethoxy)ethyl]-2-O-(2-oxopropyl)glycerol obtained in Working Example 101 was treated by following the procedure described in Working Example 69, to give 0.90 g (57%) of the above-captioned compound.

IR (Neat) cm$^{-1}$: 2930, 2860, 1720, 1465, 1120.
NMR (90 MHz, CDCl$_3$)δ: 0.87(3H), 1.27(26H), 1.53(2H), 2.15 (3H), 2.27(6H), 2.49(4H), 3.32–3.67(11H), 4.21(2H).

EFFECT OF THE INVENTION

Effect of the present invention is explained in detail by est Examples. The structural formulas of the reference compounds used are shown in the following. Reference compound IV

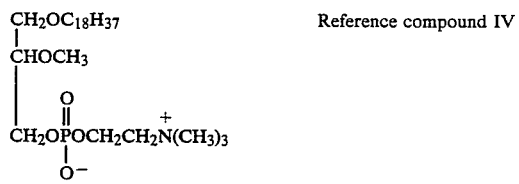

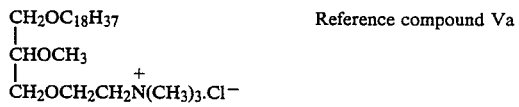

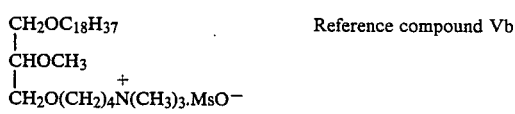

In the formulas shown above MsO$^-$ means methanesulfonate (mesylate).

TEST EXAMPLE 1

Antitumor action of the compounds in Working Examples

ICR mice (a group consisting of five mice) were inoculated intraperitoneally with 1×10$^5$ Sarcoma 180 cells per mouse, and then given intraperitoneally 0.33 mg/mouse of a compound dissolved in physiological saline, three times, i.e. 1 hour, 1 day and 2 days after inoculation. Reference compound IV, Va or Vb was given to mice under the same conditions. Shown in Table 1 are the life-span prolongation ratio against the untreated control group and the number of survived mice on the 40th day after the initiation of the test.

TABLE 1

| Test compound | Life-span prolongation ratio (T/C, %)*[1] | No. of survivors/ No. of mice tested |
| --- | --- | --- |
| Compound of Example 8 | — | 5/5 |
| Compound of Example 9 | 247 | 1/5 |
| Compound of Example 15 | 291 | 4/5 |
| Compound of Example 24 | 262 | 3/5 |
| Compound Va | 241 | 1/5 |
| Compound Vb | 291 | 0/5 |
| Compound IV | 162 | 0/5 |

*[1] only related to mice found dead

TEST EXAMPLE 2

Antitumor action of the compound of Working Example 8

ICR mice (a group consisting of 5 mice) were inoculated subcutaneously with 1×10$^6$ Sarcoma 180 cells per mouse, and given intravenously 0.03 mg/mouse or 0.3 mg/mouse of the compound of Working Example 8 dissolved in physiological saline 9 times in total, i.e. 8, 9, 10, 13, 14, 15, 16, 17, and 20 days after inoculation. The Reference compound (IV), 0.3 mg/mouse, was given under the same conditions. After 21 days, the tumor tissue was extirpated and the tumor weight was weighed. Shown in Table 2 is tumor proliferation inhibition ratio as compared with the untreated control group.

TABLE 2

| Test compound | Dose (mg/mouse) | Inhibition ratio (1-T/C) (%) |
|---|---|---|
| Compound of Example 8 | 0.03 | 65 |
| Compound of Example 8 | 0.3 | 65 |
| Compound (IV) | 0.3 | 58 |
| Control group | 0 | 0 |

TEST EXAMPLE 3

Antitumor action of the compound of Working Example 8

C3H mice (a group consisting of 5 mice) were inoculated intraperitoneally with $1 \times 10^4$ mouse mammary carcinoma cells MM46 per mouse, and given 0.25 mg/mouse of the compound of Working Example 8 dissolved in physiological saline once a day for 4 consecutive days starting from the second day after the inoculation. The Reference compound (IV) was given under the same conditions. Shown in Table 3 are the life-span prolongation ratio against the untreated control group and the number of survived mice on the 40th day after initiation of the test.

TABLE 3

| Test compound | Life-span prolongation ratio (T/C, %)*[1] | No. of survivors/ No. of mice tested |
|---|---|---|
| Compound of Example 8 | (—) | 5/5 |
| Compound IV | 155 | (0/5) |
| Control group | 100 | (0/5) |

*[1]Survivors are not included in calculations of % T/C.

TEST EXAMPLE 4

ICR mice were given intraperitoneally 1 mg of a solution (concentration: about 0.5%) of a compound of a Working Example dissolved in physiological saline. The number of survived mice 3 days after is shown in Table 4.

TABLE 4

| Test compound | Acute toxicity No. of survivors/No. of mice tested |
|---|---|
| Compound of Example 8 | 5/5 |
| Compound of Example 9 | 4/5 |
| Compound of Example 12 | 5/5 |
| Reference compound Va | 0/5 |
| Reference compound Vb | 1/5 |

TEST EXAMPLE 5 [Test Method]

Blood was collected directly from a male rabbit, using a syringe containing 3.15% of citric acid (at a ratio of 1 part to 9 parts of blood) as an anticoagulant, and centrifuged at 800 rpm for 10 minutes at room temperature to obtain platelet rich plasma (PRP). The remaining blood was centrifuged further at 3000 rpm for 10 minutes to obtain platelet poor plasma (PPP) as the supernatant. By dilution of PRP with PPP, the platelet count was adjusted to about 500,000 cells/µl. After 250 µl of the resulting PRP was stirred at 37° C. for 2 minutes, a certain amount of the test compound was added, and the mixture was stirred for further 2 minutes, and then $1 \times 10^{-8}$ M of PAF was added. Platelet aggregation was measured by using a platelet aggregometer (manufactured by Rika Denki Co. in Japan). The aggregation-inhibiting activity of a test compound was determined from the inhibition ratio against maximal transmittance (maximal aggregation ratio) caused by PAF in the control PRP. The results are shown in Table 5.

TABLE 5

| Test compound | Concentration and inhibition ratio (%) | | |
|---|---|---|---|
| | $3 \times 10^{-7}$ M | $3 \times 10^{-6}$ M | $3 \times 10^{-5}$ M |
| Compound of Example 8 | 18 | 38 | 100 |
| Compound of Example 9 | 3 | 66 | 100 |
| Compound of Example 15 | — | 43 | 100 |
| Compound of Example 24 | — | 63 | 100 |
| Compound IV | 0 | 0 | 0 |
| Compound Va | 0 | 0 | 27 |
| Compound Vb | 0 | 5 | 97 |

TEST EXAMPLE 6

Antitumor action of the compounds of Working Examples

ICR mice (a group consisting of five mice) were inoculated intraperitoneally with $1 \times 10^5$ Sarcoma 180 cells per mouse, and then given intraperitoneally 0.33 mg/mouse of a compound dissolved in physiological saline, three times, i.e. 1 hour, 1 day and 2 days after inoculation. Shown in Table 6 are the life-span prolongation ratio against the untreated control group and the number of survived mice on the 60th day after the initiation of the test.

TABLE 6

| Test compound | Life-span prolongation ratio (T/C)*[1] | No. of survivors/ No. of mice tested |
|---|---|---|
| Compound of Example 12 | 292 | 2/5 |
| Compound of Example 24 | 302 | 0/5 |
| Compound of Example 26 | 295 | 0/5 |
| Compound of Example 29 | 220 | 3/5 |
| Compound of Example 42 | 340 | 0/5 |
| Compound of Example 43 | 323 | 1/5 |
| Compound of Example 47 | 237 | 1/5 |
| Compound of Example 51 | 295 | 0/5 |
| Compound of Example 59 | 224 | 0/5 |
| Compound of Example 66 | 235 | 0/5 |

*[1]Survivors on day 60 are not included in calculations of % T/C.

TEST EXAMPLE 7

Antitumor action of the compounds of Working Examples

ICR mice (a group consisting of 5 mice) were inoculated subcutaneously with $1 \times 10^5$ Sarcoma 180 cells per mouse, and given intravenously 0.3 mg/mouse of a compound of a Working Example dissolved in physiological saline 9 times in total, i.e. 8, 9, 10, 13, 14, 15, 16, 17, and 20 days after inoculation. After 21 days, the tumor tissue was extirpated and the tumor weight was weighed. Shown in Table 7 is tumor proliferation inhibition ratio as compared with the untreated control group.

TABLE 7

| Test compound | Dose (mg/mouse) | Inhibition ratio (1-T/C) (%) |
|---|---|---|
| Compound of Example 24 | 0.3 | 78 |
| Compound of Example 26 | 0.3 | 60 |
| Control group | 0 | 0 |

TEST EXAMPLE 8

Antitumor action of the compounds of Working Examples

C3H mice (a group consisting of 5 mice) were inoculated intraperitoneally with $1 \times 10^4$ mouse mammary carcinoma cells MM46 per mouse, and given 0.25 mg/mouse of a compound of a Working Example dissolved in physiological saline once a day for 4 consecutive days starting from the second day after inoculation. Shown in Table 8 are the life-span prolongation ratio against the untreated control group and the number of survived mice on the 60th day after initiation of the test.

TABLE 8

| Test compound | Dose (mg/mouse) | Life-span prolongation ratio (T/C, %)[*1] | No. of survivors/ No. of mice tested |
|---|---|---|---|
| Compound of Example 8 | 0.125 | 144 | 2/5 |
|  | 0.25 | 315 | 3/5 |
| Compound of Example 12 | 0.125 | 206 | 4/5 |
|  | 0.25 | 126 | 3/5 |
|  | 0.5 | — | 5/5 |
| Control group | 0 | 100 | 0/5 |

[*1] Only related to the survival days of mice found dead

TEST EXAMPLE 9

Antitumor action of the compounds of Working Examples 8 and 24

ICR mice (a group consisting of 5 mice) were inoculated subcutaneously at the dorsolateral area with $1 \times 10^6$ Sarcoma 180 cells per mouse, and given orally 0.3 mg/mouse of the compound of Example 8 or the compound of Example 24 eight times in total, i.e. 8th, 9th, 10th, 13th, 14th, 15th, 16th, and 17th day after inoculation. After 20 days the tumor tissue was extirpated and the tumor weight was weighed. Shown in Table 9 is tumor proliferation inhibition ratio against the untreated control.

TABLE 9

| Test compound | Weight of tumor (g) | Inhibition ratio (%) |
|---|---|---|
| Control group | 1.38 ± 0.27 | 0 |
| Compound of Example 8 | 0.35 ± 0.04 | 75 |
| Compound of Example 24 | 0.35 ± 0.15 | 75 |

What is claimed is:

1. A compound of the formula:

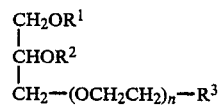

wherein $R_1$ is a $C_{8-22}$ alkyl group which may be substituted by (i) $C_{3-8}$ cycloalkyl, (ii) phenyl being unsubstituted or substituted by $C_{1-4}$ alkyl, $C_{1-4}$ alkoxy, hydroxy, nitro or halogen, (iii) halogen, (iv) cyano, (v) ethynyl, (vi) 1 propynyl, (vii) oxo or (viii) $C_{1-4}$ alkoxy, or a group represented by the formula: $-(CH_2)_m-(CQ_2)_p-CQ_3$ wherein Q is halogen, m and p are independently an integer of 0 or more and m+p is 7 to 21; $R^2$ is (i) hydrogen, (ii) a $C_{1-5}$ alkyl group which may be substituted by $C_{2-4}$ alkanoyl, carboxyl group which may be substituted by $C_{2-4}$ alkanoyl or (iv) an N-($C_{1-4}$ alkyl)thiocarbamoyl; $R^3$ is a group represented by the formula:

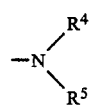

wherein $R^4$ and $R^5$ are independently hydrogen of a $C_{1-5}$ alkyl group, or $R^4$ and $R^5$ taken together with the adjacent nitrogen atom form pyrrolidino, piperidino, piperazino or morpholino, each of said groups being unsubstituted or substituted by $C_{1-4}$ alkyl, hydroxy, hydroxyethyl, aminoethyl, carbamoyl or ureido, or a group represented by the formula:

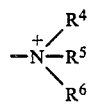

wherein $R^4$, $R^5$ and $R^6$ are independently hydrogen or a $C_{1-5}$ alkyl group, or

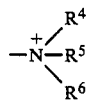

means a cyclic ammonium group chosen from the group consisting of pyridinio, oxazolio, thiazolio, pyridazinio, quinolinio, isoquinolinio, 1-($C_{1-4}$alkyl)pyrrolidino, 1-($C_{1-4}$ alkyl)piperidinio, N-($C_{1-4}$ alkyl)morpholinio or 1-($C_{1-4}$ alkyl piperazinio, each of said groups being unsubstituted or substituted by $C_{1-4}$ alkyl, hydroxy, hydroxethyl, aminoethyl, carbamoyl or ureido; and n is 2 or 3 or a pharmaceutically acceptable salt thereof.

2. The compound as claimed in claim 1, wherein $R^1$ is a $C_{12-20}$ alkyl group which may be substituted by $C_{3-8}$ cycloalkyl or halogen.

3. The compound as claimed in claim 1, wherein $R^1$ is n-octadecyl.

4. The compound as claimed in claim 1, wherein $R^2$ is a $C_{1-5}$ alkyl group.

5. The compound as claimed in claim 1, wherein $R^3$ is tri-$C_{1-5}$ alkylammonium group.

6. The compound as claimed in claim 1, which is 2-[2-[2-methoxy-3-(octadecyloxy)propyloxy]ethoxy]ethyltrimethylammonium chloride.

* * * * *

UNITED STATES PATENT AND TRADEMARK OFFICE
CERTIFICATE OF CORRECTION

PATENT NO. : 4,889,953

DATED : December 26, 1989

INVENTOR(S) : Keizo INOUE et al.

It is certified that error appears in the above-identified patent and that said Letters Patent is hereby corrected as shown below:

Please correct claim 1 as follows:

Column 48, line 16 (line 10 after the first formula), amend "carboxyl group which may be substituted" to --carboxyl, carboxylato, oxiranyl or halogen, (iii) a $C_{2-4}$ alkanoyl group which may be substituted--;

Column 48, line 25 (line 1 after the second formula), amend "hydrogen of" to --hydrogen or--;

Column 48, lines 53-54 (lines 7-8 after the fourth formula), amend "hydroxethyl" to --hydroxyethyl--.

Signed and Sealed this

Fifth Day of March, 1991

Attest:

HARRY F. MANBECK, JR.

*Attesting Officer*      *Commissioner of Patents and Trademarks*